US012649063B2

(12) United States Patent
Assambo et al.

(10) Patent No.: US 12,649,063 B2
(45) Date of Patent: Jun. 9, 2026

(54) STIMULATION GENERATOR

(71) Applicant: Capri Medical Limited, Dublin (IE)

(72) Inventors: Cédric Assambo, Dublin (IE); Tim Ring, Dublin (IE); Mike O'Keeffe, Dublin (IE); Farhat Abbas, Dublin (IE); John Mullins, Dublin (IE); Fergal Ward, Dublin (IE); Muhammad Usman, Dublin (IE)

(73) Assignee: Capri Medical Limited, Dublin (IE)

( * ) Notice: Subject to any disclaimer, the term of this patent is extended or adjusted under 35 U.S.C. 154(b) by 252 days.

(21) Appl. No.: 18/267,002

(22) PCT Filed: Dec. 15, 2021

(86) PCT No.: PCT/EP2021/086025
§ 371 (c)(1),
(2) Date: Jun. 13, 2023

(87) PCT Pub. No.: WO2022/129247
PCT Pub. Date: Jun. 23, 2022

(65) Prior Publication Data
US 2024/0058608 A1      Feb. 22, 2024

(30) Foreign Application Priority Data

Dec. 15, 2020    (EP) .................................... 20214017

(51) Int. Cl.
*A61N 1/36*          (2006.01)
(52) U.S. Cl.
CPC ..... *A61N 1/36125* (2013.01); *A61N 1/36153* (2013.01); *A61N 1/36175* (2013.01)

(58) Field of Classification Search
CPC ........................ A61N 1/36125; A61N 1/36175
See application file for complete search history.

(56) References Cited

U.S. PATENT DOCUMENTS

2016/0008602 A1      1/2016  Perryman et al.
2016/0256689 A1      9/2016  Vallejo et al.
(Continued)

FOREIGN PATENT DOCUMENTS

WO          2020227390 A1    11/2020

OTHER PUBLICATIONS

Extended European Search Report in EP Application No. 20214017.4 dated Jun. 9, 2021 (7 pages).
(Continued)

*Primary Examiner* — William J Levicky
(74) *Attorney, Agent, or Firm* — ArentFox Schiff LLP

(57) ABSTRACT

The present invention relates to a stimulation generator suitable for use in an implantable neurostimulator, including an injectable neurostimulator. The stimulation generator is adapted to provide a configurable stimulation signal comprising a component, such as a pulse. The stimulation generator comprises circuitry to receive and combine an amplitude control signal and a duty cycle signal to produce a preliminary output voltage signal which includes the component of the stimulation signal. It further comprises a voltage-controlled current source adapted to be driven by the preliminary output voltage signal; and a mode selector controlled by a stimulation mode signal to output the component from the preliminary output voltage signal as a current-controlled component of the stimulation signal via the voltage-controlled current source or as a voltage-controlled component of the stimulation signal.

19 Claims, 19 Drawing Sheets

(56) References Cited

U.S. PATENT DOCUMENTS

| | | | |
|---|---|---|---|
| 2018/0028812 A1 | 2/2018 | Vallejo et al. | |
| 2018/0250513 A1 | 9/2018 | Vallejo et al. | |
| 2018/0289965 A1 | 10/2018 | Nelson et al. | |
| 2018/0353758 A1 | 12/2018 | Vallejo et al. | |
| 2020/0046974 A1 | 2/2020 | Ostroff et al. | |
| 2020/0061381 A1* | 2/2020 | Greiner | A61N 1/36071 |
| 2020/0353256 A1* | 11/2020 | Vallejo | A61N 1/36071 |

OTHER PUBLICATIONS

International Search Report and Written Opinion in Application No. PCT/EP2021/086025 dated Mar. 21, 2022 (12 pages).

* cited by examiner

400

Receive Input Signals 401

Convert 402

Combine 403

Drive VCCS 404

Select Mode for Component 405

Output Stimulation Signal 406

910

Processor
952

Power
Supply
954

Stimulation
Generator
100

Electrode
956

950

STIMULATION GENERATOR

CROSS-REFERENCE TO RELATED APPLICATION

This application is a U.S. National Stage application under 35 USC 371 of co-pending International Application No. PCT/EP2021/086025, which was filed on Dec. 15, 2021, which in term claims priority to European Patent Application No. 20214017.4 filed on Dec. 15, 2020, both of which are incorporated herein by reference in their entirety.

BACKGROUND

The present disclosure relates to a stimulation generator, in particular a stimulation generator suitable for use in an injectable neurostimulator. Aspects of the invention relate to a stimulation generator, to a method for generating a stimulation signal, and to an injectable neurostimulator.

Neurostimulation is a very effective tool that may be used in the treatment of pain in patients. Neurostimulation therapies include invasive and non-invasive approaches that involve the application of electrical stimulation to drive neural function. Neurostimulation may be used as an alternative to pain medication and nerve block injections. It is associated with fewer side effects than many medications and can reduce the risk of drug dependency. Implantable neurostimulation systems that target specific deep subcortical, cortical, spinal, cranial, and peripheral nerve structures are known in the art.

Peripheral Nerve Stimulation is known to work well in areas such as post-surgical neuropathy, occipital neuralgia, and complex regional pain syndromes. More recently, it has been used in the treatment of new areas such as headaches including migraines and cluster headaches, and fibromyalgia. Peripheral Nerve Stimulation comprises placing an electrode, typically a wire-like electrode, next to one of the peripheral nerves. A trial period may be implemented during which the electrode is connected to an external device for sending stimulation signals to the electrode. If the patient and clinician are happy with the results of the trial, an internal device for generating the required stimulation signals is implanted into the patient's body.

The trial period may be based on an implanted electrode or may use a percutaneous electrode. Percutaneous Electrical Nerve Stimulation (PENS) therapy is known to be used for electrically stimulating a peripheral nerve in a patient to relieve pain. A PENS machine delivers low voltage electrical current to the peripheral nerves via a probe/s placed just under the patient's skin.

Implanted neurostimulators can offer methods for chronic pain patients to self-manage their condition at home while maintaining everyday activities for improved overall quality of life. However, existing pulse generators generally provide outputs restricted to either current-regulated stimulation or voltage-regulated stimulation, such that a given device may be of benefit to only a limited number of patients and conditions.

Implantable devices may need to be implanted in the patient in a surgical procedure, however, other devices may be sufficiently small to be injected using a suitable delivery device. Injectable devices reduce the time, complexity and recovery time for placing the device in the patient.

It is an aim of the present invention to address one or more of the disadvantages associated with the prior art.

BRIEF SUMMARY OF THE DISCLOSURE

Aspects and embodiments of the invention provide a stimulation generator, a method for generating a stimulation signal, and a neurostimulator as claimed in the appended claims.

In accordance with an aspect of the present disclosure, there is provided a stimulation generator suitable for use in an implantable neurostimulator, the stimulation generator adapted to provide a configurable stimulation signal comprising a component, the stimulation generator comprising circuitry to receive and combine an amplitude control signal and a duty cycle signal to produce a preliminary output voltage signal which includes the component of the stimulation signal; a voltage-controlled current source adapted to be driven by the preliminary output voltage signal; a mode selector controlled by a stimulation mode signal to output the component from the preliminary output voltage signal as a current-controlled component of the stimulation signal via the voltage-controlled current source or as a voltage-controlled component of the stimulation signal.

In this way, a highly configurable stimulation signal may be generated that provides a physician with a single device that facilitates a wide range of neurostimulation treatment protocols. The stimulation signal may comprise a voltage-controlled component and/or a current controlled component. The ability to select between voltage-regulated components and current-regulated components offers the possibility of delivering therapeutic solutions tailored to provide more effective responses to specific patient symptoms.

In accordance with another aspect of the present disclosure, there is provided a stimulation generator suitable for use in an injectable neurostimulator, the stimulation generator adapted to provide a configurable periodic stimulation signal comprising a component, the stimulation generator comprising an input configured to receive digital voltages to generate the component including digital voltages representing a stimulation mode signal to configure the component of the stimulation signal as a voltage-controlled component or a current-controlled component, an amplitude control signal to control the amplitude of the component of the stimulation signal, a duty cycle signal to control the duration of the component of the stimulation signal, a converter to convert the amplitude control signal to an analog signal, a combining module to combine the duty cycle signal with the analog signal to provide a preliminary output voltage signal which includes the component of the stimulation signal, a voltage-controlled current source adapted to be driven by the preliminary output voltage signal; a mode selector adapted to be controlled by the stimulation mode signal to output the component from the preliminary output voltage signal as a current-controlled component of the stimulation signal via the voltage-controlled current source or as a voltage-controlled component of the stimulation signal.

In this way, a highly configurable neurostimulation signal can be provided in a manner than can be implemented in an injectable form factor. The stimulation signal is configurable in its period, amplitude, component/pulse width, duty cycle and signal regulation mode e.g. a voltage-controlled signal or a current-controlled signal. The stimulation generator is configured to provide the stimulation signal based on a limited number of data inputs. This is particularly useful in allowing for implementation of the stimulation signal in neurostimulation device for delivery by injection. Injectable devices are useful in that they can be inserted quickly and conveniently, with reduced trauma.

In an example, the stimulation generator is adapted to provide a configurable periodic stimulation signal comprising a plurality of components. The plurality of components may include a voltage-controlled component and a current-controlled component. The component may be a pulse.

The period of the stimulation signal may be in the range 2.5 μs to 2 ms. The component may have a duration of between 1.25 μs and 2 ms. The amplitude of the stimulation signal can change at a rate of up to 25 kHz. The mode of the stimulation signal can change at a rate of up to 400 kHz. A current-controlled component may have an amplitude of up to ±15 mA. A voltage-controlled component may have an amplitude of up to ±15 V.

The stimulation generator may comprise a stimulation output to output the stimulation signal.

Optionally, the duty cycle signal is derived from an enable signal and a pulse pattern signal. The duty cycle signal may be derived from a 2:1 multiplexor having ground and the pulse pattern signal as inputs and the enable signal as a selecting input. The duty cycle signal may be derived via the output difference amplifier circuit, comprising an op-amp.

In an example, the input is configured to receive the digital voltages to generate the component in parallel.

In an example, at least one of the stimulation mode signal, amplitude control signal, enable signal and pulse pattern signal is a unipolar binary signal. The unipolar binary signal may have a nominal low value of 0 V and a nominal high value of between 0.8 V and 5 V. In an example, the nominal high value is 3.3 V.

The duty cycle signal may be a bipolar signal. The pulse pattern signal may be converted to a bipolar signal.

Optionally, the duty cycle signal and the analog signal are scaled to have a maximum magnitude of 1 volt prior to being input to the combining module. The duty cycle signal and the analog signal may be attenuated prior to being input to the combining module, or may be amplified. The output of the combining module may be amplified to provide the preliminary output voltage signal.

In an example, the combining module is an analog multiplier, and may be a four-quadrant multiplier.

Optionally, the stimulation generator comprises a noise input signal adapted to introduce stochastic noise to the stimulation signal. The noise input signal is an input to the combining module. Where the combining module is an analog multiplier, the noise input signal may be applied to a scale adjust input thereof.

In an example, the voltage controlled current source is a Howland current pump.

The converter unit may comprise at least one of an integrator circuit such as an op-amp integrator, a low pass filter, and/or an RMS-to-DC converter.

Optionally, the stimulation generator comprises a current management module for managing an output current of the stimulation signal. The current management module may be located between the mode selector and the stimulation output. The current management module is adapted to generate an active low fault flag to a microcontroller if the output current is outside a predefined range. The current management module may comprise a fuse, wherein the fuse may be polyfuse. The current management module may comprise current limiting resistors.

In accordance with a further aspect of the present disclosure, there is provided a method for generating a stimulation signal for use in neurostimulation. The method comprises receiving digital voltages for generating the component including digital voltages representing a stimulation mode signal to configure the component of the stimulation signal as a voltage-controlled component or a current-controlled component, an amplitude control signal to control the amplitude of the component of the stimulation signal, a duty cycle signal to control the duration of the component of the stimulation signal; converting the amplitude control signal to an analog signal; combining the duty cycle signal with the analog signal to provide a preliminary output voltage signal which includes the component of the stimulation signal; driving a voltage-controlled current source by the preliminary output voltage signal; outputting the component from the preliminary output voltage signal as a current-controlled component of the stimulation signal via the voltage-controlled current source or as a voltage-controlled component of the stimulation signal, based on the stimulation mode signal.

In accordance with a still further aspect of the present disclosure, there is provided an injectable neurostimulator comprising a processor, a power supply, an electrode, and the stimulation generator described herein.

It is desirable to provide systems and methods which offer a wider range of electrical output modes as well as a variety of pulse patterns that can be combined with controlled noise signal of adjustable signal to noise ratio.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

BRIEF DESCRIPTION OF THE DRAWINGS

Embodiments of the invention are further described hereinafter with reference to the accompanying drawings, in which.

DETAILED DESCRIPTION

Figure 1:
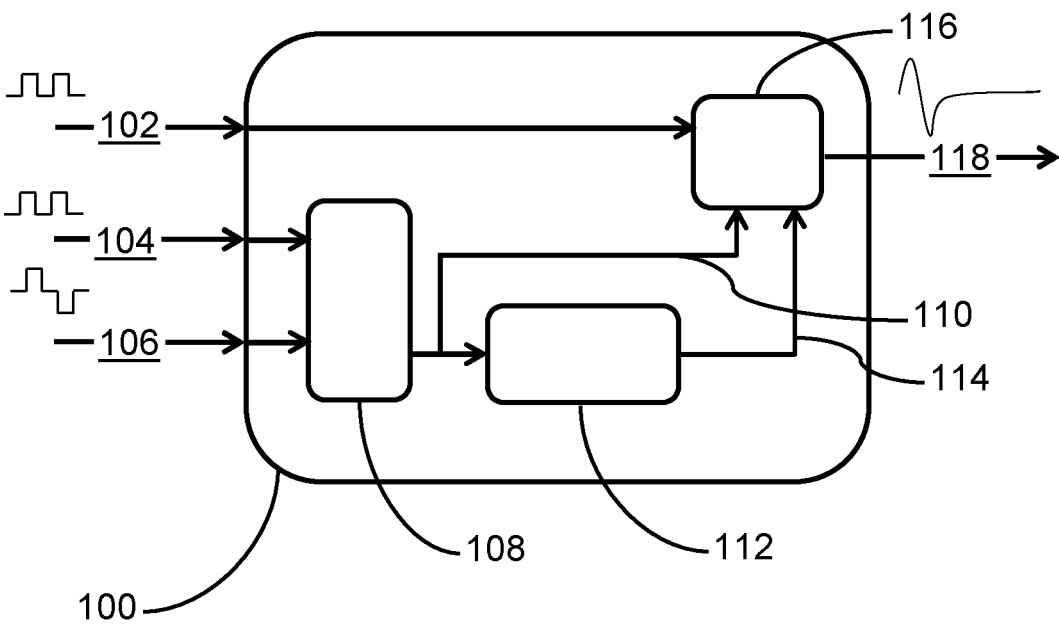
FIG. 1 is a block diagram of an example stimulation generator according to the disclosure.

Referring to FIG. 1, there is shown a block diagram of an example stimulation generator 100 according to the present disclosure. The stimulation generator 100 is suitable for use in an implantable neurostimulator, and may be suitable for an injectable neurostimulator. Injectable neurostimulators can be located at the desired location in a patient via injection. The stimulation generator 100 is adapted to provide a configurable stimulation signal. The stimulation generator 100 receives three input signals comprising a stimulation mode signal 102, an amplitude control signal 104, and a duty cycle signal 106. The stimulation generator 100 comprises circuitry to combine a number of digital inputs to create a full-scale amplitude-modulated signal of configurable polarity. The stimulation generator 100 comprises circuitry 108 to combine the amplitude control signal 104 and the duty cycle signal 106 to produce a preliminary output voltage signal 110. The circuitry 108 may comprise a converter (not shown) to convert the amplitude control signal to an analog signal and a combining module (not shown) to combine the duty cycle signal with the analog signal. The preliminary output voltage signal 110 includes a component of the stimulation signal. The stimulation generator 100 further comprises a voltage-controlled current source 112 which is driven by the preliminary output voltage signal 110 and outputs a preliminary output current signal 114. The preliminary output voltage signal 110 and preliminary output current signal 114 are provided as inputs to a mode selector 116, whose operation is controlled by the stimulation mode signal 102. Depending on the value of the stimulation mode signal, the mode selector outputs the component from the preliminary output voltage signal 110 as a current-controlled component of the stimulation signal via the voltage-controlled current source or as a voltage-controlled component of the stimulation signal.

In this way, the stimulation generator 100 provides a stimulation signal having a desired period and a component or components of desired amplitude, polarity, duration, duty cycle, and mode, wherein the modes available are either voltage-controlled or current controlled. Thus, the stimulation signal is highly configurable, and the stimulation generators of the disclosure provide the ability to generate a wide variety of components within a stimulation signal. The stimulation signal may comprise a combination of one or more voltage-controlled components and one or mode current-controlled components. In this way, a physician can offer a large number of treatment programs with one device, wherein treatment programs may comprise component combinations and configurations not previously available. The stimulation generators disclosed herein allow more patients and conditions to be treated by the same device.

Each of the stimulation mode signal 102 and amplitude control signal 104 may be a unipolar binary signal, such as may be output by a microcontroller. An example diagram of such a binary signal is shown beside the stimulation mode signal 102 and amplitude control signal 104. An example "high" voltage in these signals may be a nominal 3.3 volts, however other voltages may be used, for example, signals having a nominal high voltage of 0.8 volts, 1.5 volts. 1.8 volts, 2.5 volts or 5 volts or other suitable voltage may be used with the stimulation generator.

The amplitude control signal 104 may be a Pulse Width Modulation (PWM) signal. The circuitry 108 may convert the amplitude control signal 104 into an analog signal. The amplitude of the analog signal may be used to control the amplitude of the component(s) of the stimulation signal 118. The circuitry 108 may include an op-amp integrator, low pass filter or other suitable module to convert the amplitude control signal 104 to the analog signal.

The duty cycle signal 106 may be a bipolar signal. The duty cycle 106 signal may be derived from a pulse pattern signal (not shown) and enable signal (not shown), each of which may be a unipolar binary signal. The amplitude control signal 104 may be converted to an analog signal by the circuitry 108 and then combined with the duty cycle signal 106 to create the preliminary output voltage signal 110. The preliminary output voltage signal 110 comprises full-scale amplitude modulated bipolar components. Components of the preliminary output voltage signal and stimulation signal may take the form of a pulse, and may also include variations in the signal having gradual rise and/or fall times.

The stimulation signal 118 may be a periodic signal. It may comprise a single component per period, or it may comprise more than one component per period. Each component may be a voltage-controlled component or a current-controlled component. For a periodic signal comprising more than one component, each period may comprise one or more voltage-controlled components and one or more current-controlled components. The stimulation signal is not limited to a periodic signal, and may alternatively be a non-periodic arbitrary waveform. An example bipolar stimulation signal is shown beside the output of the stimulations signal 118.

The period of the stimulation signal may be as low as 2.5 μs, with a component duration as low as 1.25 μs. The amplitude of the stimulation signal can change at a rate of up to 25 kHz. The mode of the stimulation signal may change at a rate of up to 400 kHz. The amplitude and regulation mode of the stimulation signal can change at a faster rate than the minimum pulse width. This capability makes it possible to generate arbitrary waveforms without the constraint of periodicity.

The stimulation signal may be a biphasic, monophasic or pseudo biphasic signal. A biphasic signal is one wherein for each positive component in a period, there is also a component of equal shape and magnitude but opposite polarity, such that there is symmetry between the components in the period. A monophasic signal only has components of one polarity. A pseudo-biphasic signal has components that have equal magnitude but opposite polarity when averaged over the period of the signal, such that opposite polarity components may be of different shapes. Biphasic and pseudo-biphasic signals may be referred to as balanced.

In another example, the mode selector 116 is placed immediately downstream of the circuitry. In this way, when the voltage-regulated output mode is selected, the preliminary output voltage signal is applied to the load. When the current-regulated output mode is selected, the preliminary output voltage signal from the mode selector 116 is applied to the input to the voltage-controlled current source 112. An additional switch or selector may be included to provide to prevent reverse current flow while in voltage-regulated mode.

Figure 2:
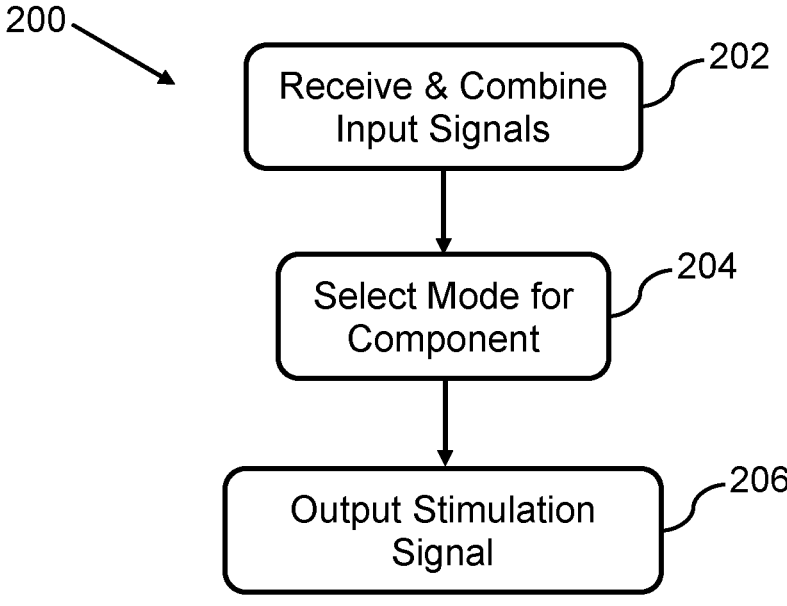
FIG. 2 is a block diagram of a method for generating a stimulation signal according to the disclosure.

Referring now to FIG. 2, there is shown a flow diagram of a method 200 of generating a stimulation method according to the present disclosure. The method 200 of FIG. 2 may be carried out by the stimulation generator 100 of FIG. 1, but is not limited thereto. The method 200 comprises, at block 202, receiving and combining an amplitude control signal and a duty cycle signal to produce a preliminary output voltage signal, where the preliminary output voltage signal includes a component of a stimulation signal. At block 204, the method comprises selecting whether the component to be output is a voltage-controlled component or current-controlled component. The selecting may comprise receiving a stimulation mode signal. At block 206, the method comprises outputting the stimulation signal including the component as a current-controlled component or as a voltage-controlled component. The component or components of the stimulation signal are configured according to the amplitude control signal and the duty cycle signal.

Figure 3:
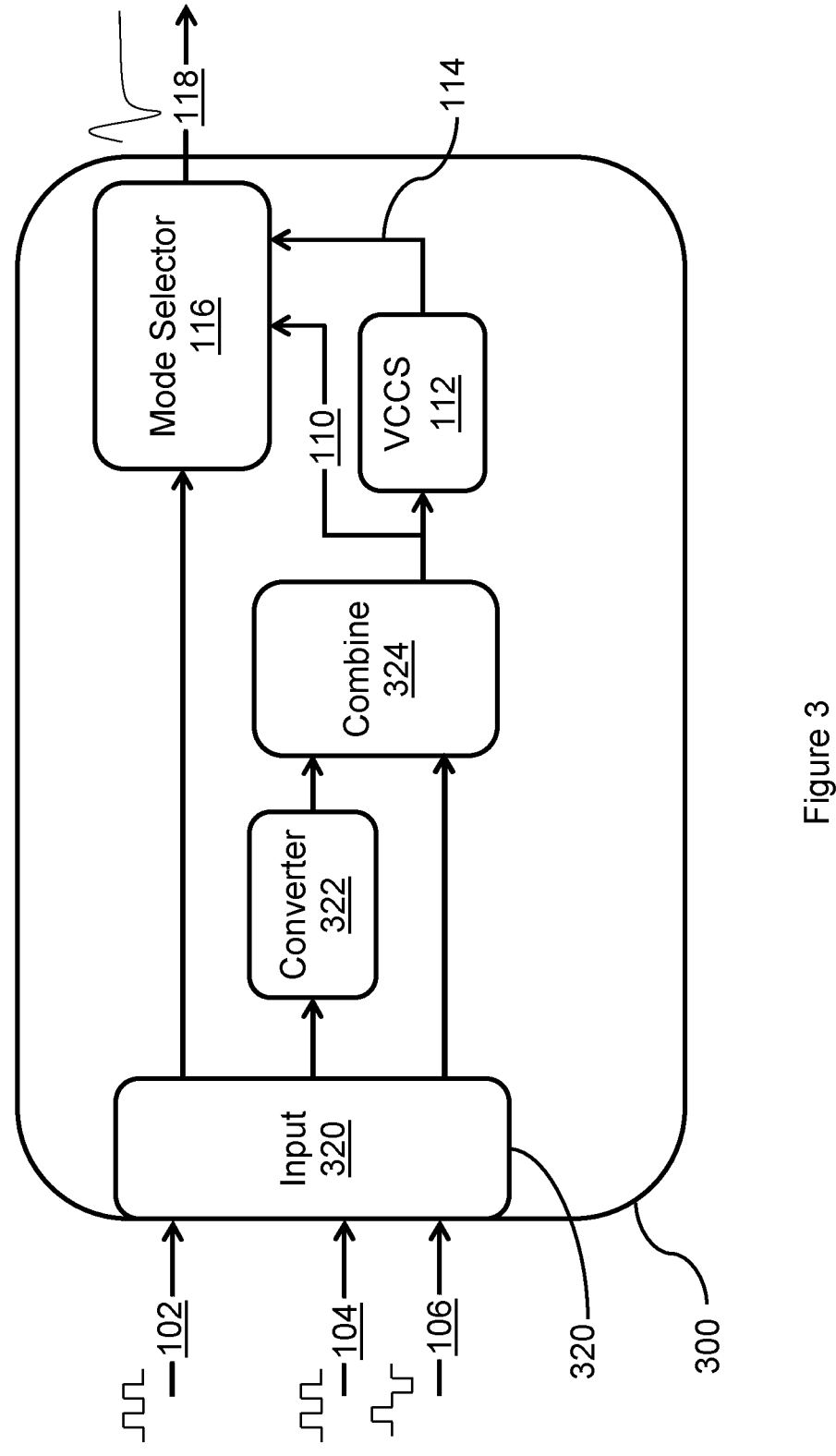
FIG. 3 is a block diagram of a further example stimulation generator according to the disclosure.

Referring now to FIG. 3, there is shown a block diagram of another example of stimulation generator 300 according to the present disclosure. The stimulation generator 300 of FIG. 3 is similar to the stimulation generator 100 described in relation to FIG. 1, and the same reference numerals are used for the same parts where appropriate. Certain common features in the examples described in relation to FIGS. 1 and 3 are not explained in detail again here. It will be understood that the operation and advantages of the stimulation generation 100 can also be applied to the stimulation generator 300. The stimulation generator 300 is suitable for use in an implantable neurostimulator, in particular an injectable neurostimulator. In order to be suitable for use in an injectable device, it will be understood that the stimulation generator is implementable in a suitably small form factor. The stimulation generator disclosed herein may be implemented to have a width of between about 0.5 millimetres and about 5 millimetres, for example between about 1 millimetre and about 3 millimetres, and a length of up to about 10 millimetres, for example up to about 5 millimetres.

The stimulation generator 300 is adapted to provide a configurable periodic stimulation signal comprising a component. The stimulation signal is not required to be periodic and the stimulation generator 300 can provide a configurable non-periodic stimulation signal. The component or components of the stimulation signal may take the form of a pulse, and/or may be shaped to have slower raise and/or fall times to provide other arbitrary signal shapes.

The stimulation generator 300 comprises an input 320 configured to receive digital voltages to generate the component. These received digital voltages include digital voltages representing a stimulation mode signal 102, an amplitude control signal 104 and a duty cycle signal 106. The stimulation mode signal 102 is used to configure the component of the stimulation signal as a voltage-controlled component or a current-controlled component. The amplitude control signal 104 is to control the amplitude of the component of the stimulation signal. The amplitude control signal 104 may be a Pulse Width Modulated (PWM) signal. The duty cycle signal 106 is to control the duration of the component of the stimulation signal. The stimulation generator 300 comprises circuitry to process the duty cycle signal 106 and amplitude control signal 104. The circuitry includes a converter 322 to convert the amplitude control signal 104 to an analog signal. The circuitry further comprises a combining module 324 to combine the duty cycle signal 106 with the analog signal to provide a preliminary output voltage signal 110 which includes the component of the stimulation signal 118. The stimulation generator 300 further comprises a voltage-controlled current source 112 adapted to be driven by the preliminary output voltage signal

110. The stimulation generator 300 further comprises a mode selector 116 controlled by the stimulation mode signal 102 to output the component from the preliminary output voltage signal as a current-controlled component of the stimulation signal via the voltage-controlled current source or as a voltage-controlled component of the stimulation signal.

The stimulation mode signal 102, amplitude control signal 104, and duty cycle signal 106 may be received from a microcontroller (not shown) adapted to control the generation of the stimulation signal. A suitable microcontroller may be one from the MAXIM MAX32600 microcontroller family, the MAXIM MAX32660 microcontroller family, or similar devices. Microcontrollers in these families may have a core operating at 24 MHz or above and so providing a 0.042 μs clock. While operation of the microcontroller outputs at higher frequencies may result in high power consumption, it is envisaged that the microcontroller outputs may operate at frequencies of 1 MHz or higher.

As with the stimulation generator 100 described in relation to FIG. 1, each of the stimulation mode signal 102 and amplitude control signal 104 may be a unipolar binary signal. An example diagram of such a binary signal is shown beside the stimulation mode signal 102 and amplitude control signal 104. An example "high" voltage in these signals is a nominal 3.3 volts, however other voltages may be used, for example, for example signals having a nominal high voltage of 0.8 volts, 1.5 volts. 1.8 volts, 2.5 volts or 5 volts or other suitable voltage may be used with the stimulation generator 300.

The input 320 may be configured to receive the signals in parallel. The input may comprise an input terminal, such as a pin or bump, for each signal.

The duty cycle signal 106 may be a bipolar digital signal. The duty cycle signal 106 may comprise pulses that correspond to the desired components of the stimulation signal. Each pulse of the duty cycle signal 106 is intended to map to a component of the stimulation signal. The duty cycle 106 signal may be derived from one or more other signals. For example, the duty cycle may be derived from a combination of a pulse pattern signal (not shown) and an enable signal (not shown). In such an example, the pulse pattern signal may provide pulses that will be used to generate the component of the stimulation signal, while the enable signal may be used to control the mark-space ratio of the stimulation signal. The pulse pattern signal may be a square wave signal. The pulse pattern signal may be combined with the enable signal in a number of ways, for example, using an op-amp comparator, or using a 2:1 multiplexor, with one input tied to ground and the enable signal as the selecting input.

Once the input signals of the stimulation mode signal 102, amplitude control signal 104, and duty cycle signal 106 have been received by the input of the stimulation generator 300, they are processed to generate a preliminary output voltage signal 110. The preliminary output voltage signal 110 is an analog signal comprising a component or components of variable polarity, amplitude, duration and mode. The amplitude of each component is variable up to full-scale.

The amplitude control signal 104 may be processed to convert it to an analog signal indicative of the desired amplitude for the component. Where the amplitude control signal 104 is a PWM signal, it may be processed by circuitry for low-pass filtering the digital signal. The amplitude control signal 104 is processed by a converter 322 to convert it convert it to an analog signal. In an example, the converter 322 comprises an op-amp integrator. The op-amp integrator may be considered to function as an "active low pass filter".

In other examples, the converter 322 may comprise a low-pass filter. The converter 322 may comprise an RMS-to-DC converter. Other mechanisms for converting the amplitude control signal 104 will be apparent to the person skilled in the art. The use of the op-amp integrator, low-pass filter, RMS-to-DC converter and the like are advantageous as they provide the digital to analog conversion without the need for a standard Digital to Analog Converter (DAC). Such DACs tend to be too large for use in an injectable device.

The analog signal derived from the amplitude control signal 104 is combined with the duty cycle signal 106 to create the preliminary output voltage signal 110. The duty cycle signal 106 and the analog signal are combined by a combining module 324. In an example, the combining module is an multiplier, such as a four-quadrant multiplier. The multiplier multiplies the duty cycle signal 106 with the analog signal. One or more of the duty cycle signal 106 and analog signals may be scaled prior to being input to the combining module 324. In an example, the input voltages to the combining module are scaled to vary between −1 V and 1 V. In this way, the magnitude of the output from the combining module 324 may be controlled to also be between 0 V and 1 V. Some voltages may be attenuated, or if the inputs to the stimulation generator were operating on a 0.8 logic voltage or other logic voltage less than 1, they would be amplified prior to input to the combining module. The output of the combining module 324 may be amplified to form the preliminary output voltage signal 110. The amplification may be carried out in a single amplification stage or in a number of separate amplification stages. In an example, the output of the combining module 110 is amplified firstly by an amplifier having a gain of 5 to provide a signal with amplitude varying from −5 V to +5 V, and then subsequently further amplified by an amplifier having a gain of 3 to provide the preliminary output voltage signal 110 with amplitude varying from −15 V to +15 V.

The preliminary output voltage signal 110 is used to drive a voltage-controlled current source 112 (VCCS). In an example, the VCCS 112 is configured to provide components corresponding to those of the preliminary output voltage signal 110, where the component of the output current may have an amplitude varying from −15 mA to +15 mA. In an example, the VCCS 112 is a Howland current pump, however it will be understood that other VCCS configurations may be used.

The preliminary output voltage signal 110 and the output of the VCCS 112, which may be referred to as a preliminary output current signal, are input to a mode selector 116. The mode selector 116 controls which signal is output as the stimulation signal, in dependence on the stimulation mode input 102. In an example, a "high" value on the stimulation mode input 102 will pass the preliminary output voltage signal 110 to be output by the stimulation generator, and a "low" value will allow the output of the VCCS 112 to be output. It will be understood that the mode selector 116 may alternatively be configured such that a "high" value on the stimulation mode input 102 will pass the output of the VCCS 112 to be output by the stimulation generator, and a "low" value will allow the output of the VCCS 112 to be output. The mode selector may be a 2:1 multiplexor. In the example where the "high" value on the stimulation mode signal 102 passes the preliminary output voltage signal 110 to be output as the stimulation signal, the preliminary output voltage signal 110 is connected to a normally open input on the multiplexor, and the output of the VCCS 112 is connected to the normally closed input thereof.

In an example, the voltage-controller current source 112 and the mode selector 116 are combined in a single module.

The stimulation generator 300 may comprise current sensing and current limiting functionality, and electrical isolation to ensure patient safety.

In use, a processor (not shown) such as a microcontroller provides the stimulation mode signal 102, amplitude control signal 104, and duty cycle signal 106 to the stimulation generator 300. These signals are produced by the microcontroller to cause a stimulation signal of desired parameters to be generated by the stimulation generator 300. The desired parameters may be provided to the microcontroller by a user via a user interface. The desired parameters may be stored in memory on the microcontroller, either before the device is placed in a patient, or subsequently. To allow for a form factor small enough to allow injection of the neurostimulator, the microcontroller may have a limited number of connections available for communicating with the stimulation generator. It is advantageous to be able to generate the desired stimulation signal based on a small number of inputs to the stimulation generator. According to the disclosure, the stimulation generator may use three or four inputs from the microcontroller to generate the stimulation signal that is highly configurable.

Typically, the stimulation mode signal 102, amplitude control signal 104, and duty cycle signal 106 are unipolar binary signals. The duty cycle signal 106 may be provided to the stimulation generator 300 as one or more unipolar signals which are then processed by the stimulation generator 300 to form a duty cycle signal 106 of variable polarity. For example, the duty cycle signal 106 may be derived from a unipolar pulse pattern signal. The pulse pattern signal may be a unipolar signal, and may be converted to a variable polarity signal before combination with the enable signal. Such a pulse pattern signal may be combined with the enable signal to form a signal having the desired shape of the stimulation signal, including components of the desired duration. The amplitude control signal 104 is converted from a digital signal to an analog signal. This may be carried out using an op-amp integrator, which provides an equivalent low-pass filtering function; or a low-pass filter. This low pass filtering- type action allows conversion of a PWM digital signal from the microcontroller to the DC equivalent amplitude set point of the component. The conversion may further comprise an RMS-to DC conversion. The analog signal is then combined with the duty cycle signal 106. The analog signal and the duty cycle signal 106 may be scaled prior to the combining operation. This scaling may comprise attenuation or amplification. The output of the combining operation is then typically amplified to form the preliminary output voltage signal 110. The preliminary output voltage signal 110 is then fed to both the mode selector 116 and the voltage controlled current source 112. The output of the voltage controlled current source 112 is then fed to the mode selector 116. The output of the mode selector 116 is controlled by the stimulation mode signal 102. This signal controls whether the preliminary output voltage signal 110 of the output of the VCS 112 is output as the stimulation signal 118.

The component referred to herein will be understood to be the basic building block of the stimulation signal. The construction of a stimulation signal and/or the component/s within the stimulation signal is dependent on a number of factors, including the switching frequency of the input signals received from the microcontroller, and the operation of analog components in the converter 322, combining module 324 and mode selector 116. At higher frequencies, the operation of the analog components in the stimulation generator 300 may reduce the reactiveness of the component in the stimulation signal to the changes in the input signals. The minimum duration of a component, which may be referred to as the pulse width where the component is a pulse, is determined by the frequency of the duty cycle signal, which may in turn be dependent on the frequency of the pulse pattern signal. The stimulation generator may switch from outputting a current-regulated component to a voltage-regulated component at the frequency of the stimulation mode signal. However, at higher frequencies, the operation of the analog components in the mode selector may introduce a delay in the mode switching. The frequency at which the amplitude of a component or components can change may be determined by the time constant of the op-amp integrator low pass filter for converting the PWM amplitude control signal 104 to an analog signal. The longer the component duration, the more impactful the effects of switching PWM parameters and stimulation mode will be on the component.

The period of the stimulation signal may be as low as 2.5 μs, with a component duration as low as 1.25 μs. The amplitude of the stimulation signal can change at a rate of up to 25 kHz. The mode of the stimulation signal may change at a rate of to 400 kHz. The amplitude and regulation mode of the stimulation signal can change at a faster rate than the minimum pulse width. This capability makes it possible to generate arbitrary waveforms without the constraint of periodicity.

Figure 4:
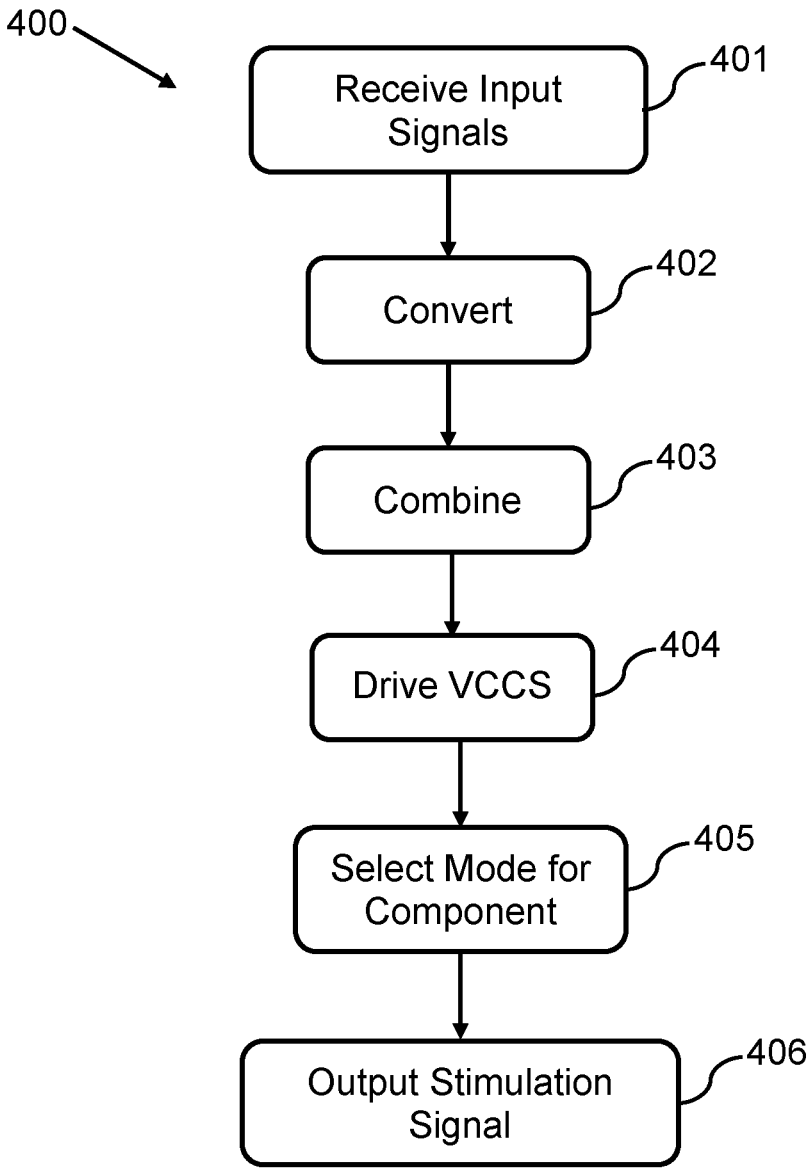
FIG. 4 is a block diagram of a further method for generating a stimulation signal according to the disclosure.

Referring now to FIG. 4, there is shown a flow diagram of a method indicated generally by the reference numeral 400. The method of FIG. 4 may be implemented by the stimulation generator as described in relation to FIG. 3, but is not limited thereto. The method comprises, at block 401, receiving digital voltages for generating a component of a stimulation signal. The digital voltages include voltages representing a stimulation mode signal, an amplitude control signal, and a duty cycle signal. The stimulation mode signal is to configure the component of the stimulation signal as a voltage-controlled component or a current-controlled component. The amplitude control signal is to control the amplitude of the component of the stimulation signal. The duty cycle signal is to control the duration of the component of the stimulation signal. In block 402, the method comprises converting the amplitude control signal to an analog signal. In block 403, the method comprises combining the duty cycle signal with the analog signal to provide a preliminary output voltage signal which includes the component of the stimulation signal. In block 404, the method comprises driving a voltage-controlled current source by the preliminary output voltage signal. In block 405, the method comprises selecting the component from the preliminary output voltage signal as a current-controlled component of the stimulation signal via the voltage-controlled current source or as a voltage-controlled component of the stimulation signal, based on the stimulation mode signal. In block 406, the method comprises outputting the stimulation mode signal. It will be understood that various blocks may be combined or may happen in parallel, and the method is not limited to the linear process as illustrated.

Figure 5:
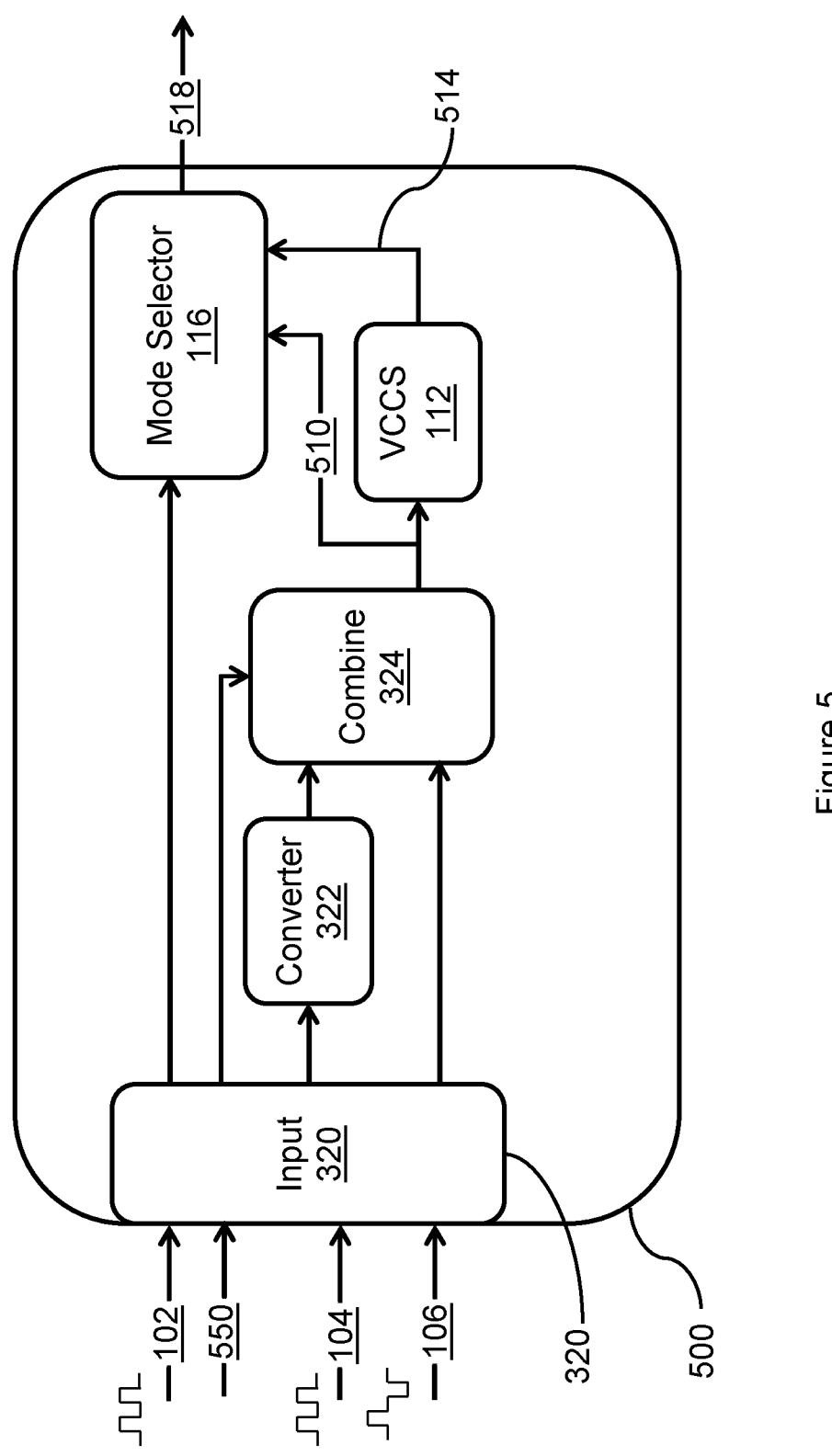
FIG. 5 is a block diagram of an example of a stimulation generator comprising a noise signal according to the disclosure.

Referring now to FIG. 5, there is shown another example of a stimulation generator 500 according to the present disclosure. The stimulation generator 500 of FIG. 5 is similar to the stimulation generator 300 described in relation to FIG. 3, as such the same reference numerals will be used for the same parts where appropriate, and they will not be described here again. The stimulation generator 500 comprises a noise input 550. The noise input may be used to add a stochastic variation to the stimulation signal. Such variations may be used to reduce therapy tolerance and habituation. Therapy tolerance and habituation occur when a neurostimulation therapy initially provides good results to a patient, but those results deteriorate over time as the nerves become accustomed to the therapy.

In the stimulation generator 500, the noise input is received at the input 320 and is then combined with the duty cycle signal 106 and the analog signal from the converter 322 in the combining module 324. The noise signal 550 maybe generated in a pseudo-random manner by the microcontroller. The frequency of the noise signal 550 should be greater than the fundamental frequency of the "clean" stimulation signal for the contribution of the noise signal to be controllable in terms of the signal to noise ratio. In an example, the combining module is an analog multiplier and the noise input is fed to the offset input of the analog multiplier to perform a summing operation. The offset input may also be referred to as a scale adjust input. The noise signal 550 may be scaled prior to input to the combining module 324, to prevent saturation. The combining module 324 thus outputs a noisy signal which is used to form a noisy preliminary output voltage signal 510. The noisy preliminary output voltage signal 510 is fed to the VCCS 112 to create a noise output therefrom, which may be referred to as a noisy preliminary output current signal 514. Thus, a noisy stimulation signal 518 is provided by the mode selector 116.

Figure 6:
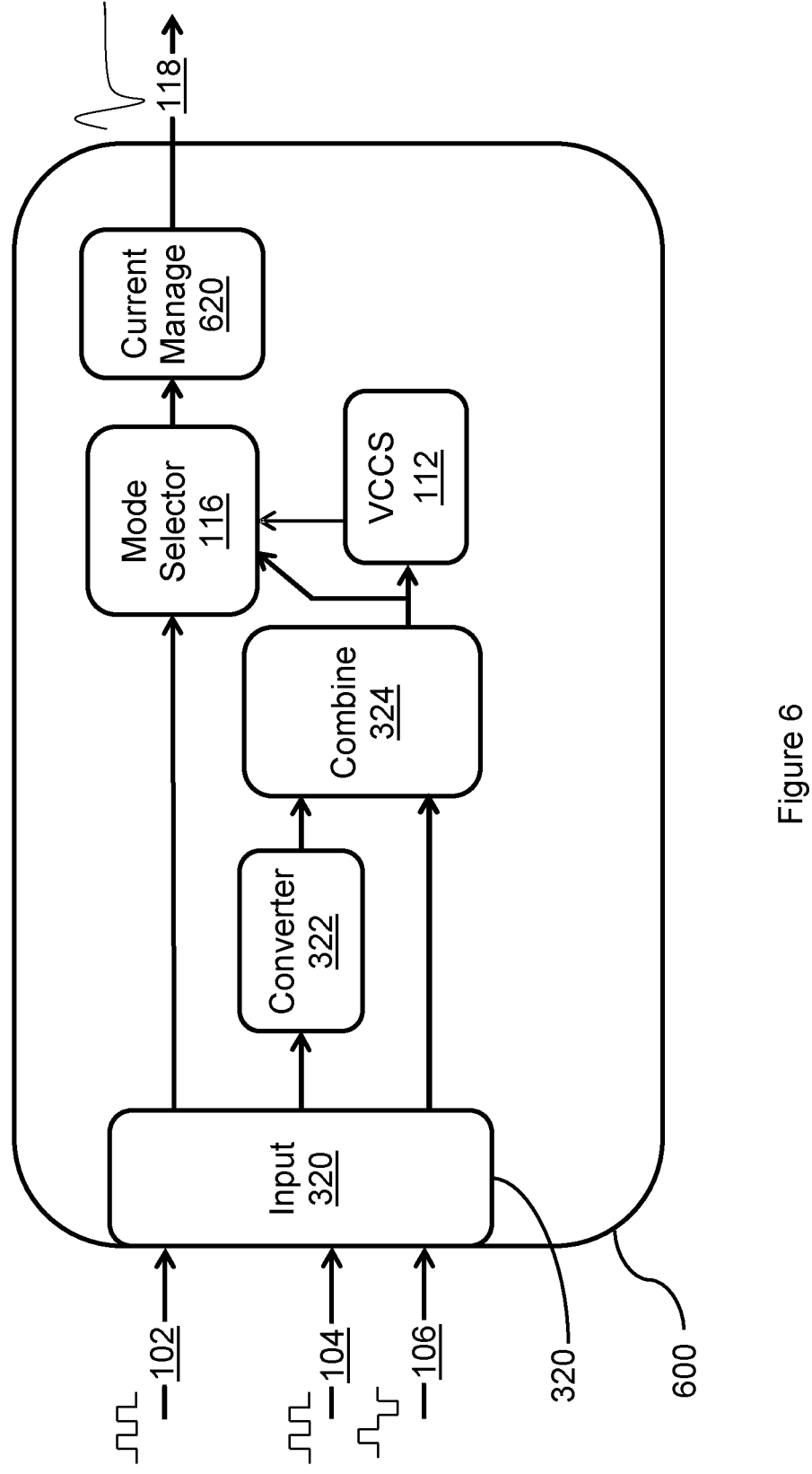
FIG. 6 is a block diagram of an example of a stimulation generator comprising current management module according to the disclosure.

Referring now to FIG. 6, there is shown another example of a stimulation generator 600 according to the present disclosure. The stimulation generator 600 of FIG. 6 is similar to the stimulation generator 300 described in relation to FIG. 3, as such the same reference numerals will be used for the same parts where appropriate, and they will not be described here again. The stimulation generator 600 comprises a current management module 620 placed after the mode selector 116, to ensure the stimulation signal 118 comprises current levels that are safe for the patient. The current management module 620 receives the stimulation signal 118 output from the mode selector and acts to monitor the output current of the stimulation generator 600. The monitored output current may be the current from the voltage-controlled current source or voltage source. The current management module 620 is adapted to generate a fault flag to the microcontroller if the output current is outside a predefined range. In an example, the fault flag is an active low fault flag. The fault flag prompts the microcontroller to take action, for example to turn off the neurostimulation. If a sequence of successive fault flags is detected by a digital counter separate from the microcontroller, which may be for example eight successive flags, then it is assumed the microcontroller may be unresponsive. In such a scenario, one of the outputs of microcontroller triggers a signal that switches the output of the neurostimulator from the patient to a known dummy load (not shown) (currently 1 kOhm) ensuring a fail-safe state in single fault condition. This mechanism ensures there is no unacceptable risk to the patient in normal conditions and in a single fault condition. It also reduces the level of criticality of the software components responsible for shutting down stimulation when an over-current condition is detected.

The current management module 620 may comprise a fuse such as a polyfuse. The current management module 620 may comprise current limited resistors. The output current will additionally be limited by the output drive current limitation intrinsic to the active devices of the stimulation generator and the output drive voltage limitation intrinsic to the active devices of the stimulation generator. If the current level exceeds 30 mA for 1 second, a resettable fuse (not shown) at the stimulation generator output will activate to stop neurostimulation.

The stimulation generator may further comprise an over-voltage limitation to restrict the voltage applied to the patient.

Figure 7:
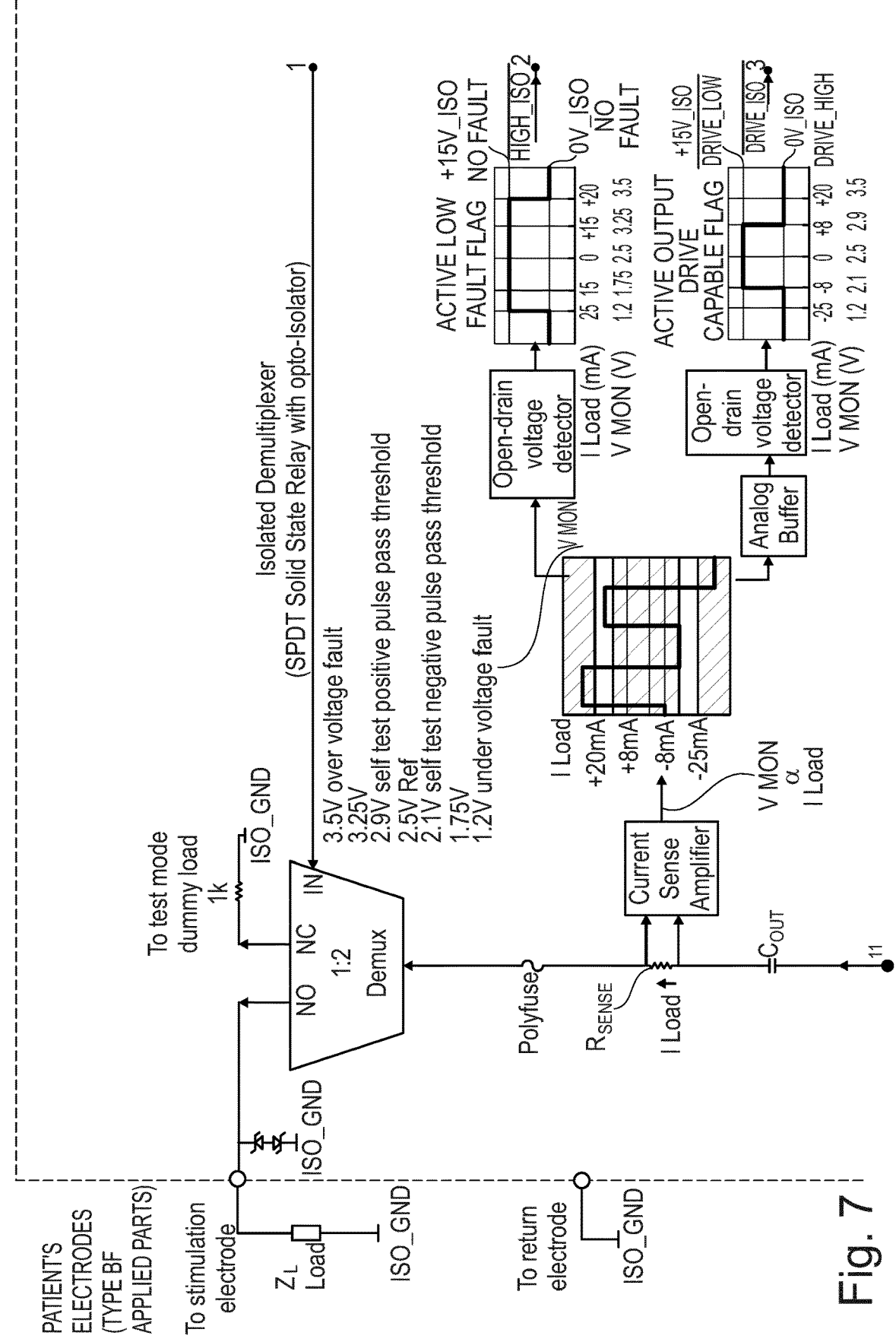
FIG. 7 is a high-level circuit schematic of an example stimulation generator according to the disclosure.
Figure 7:
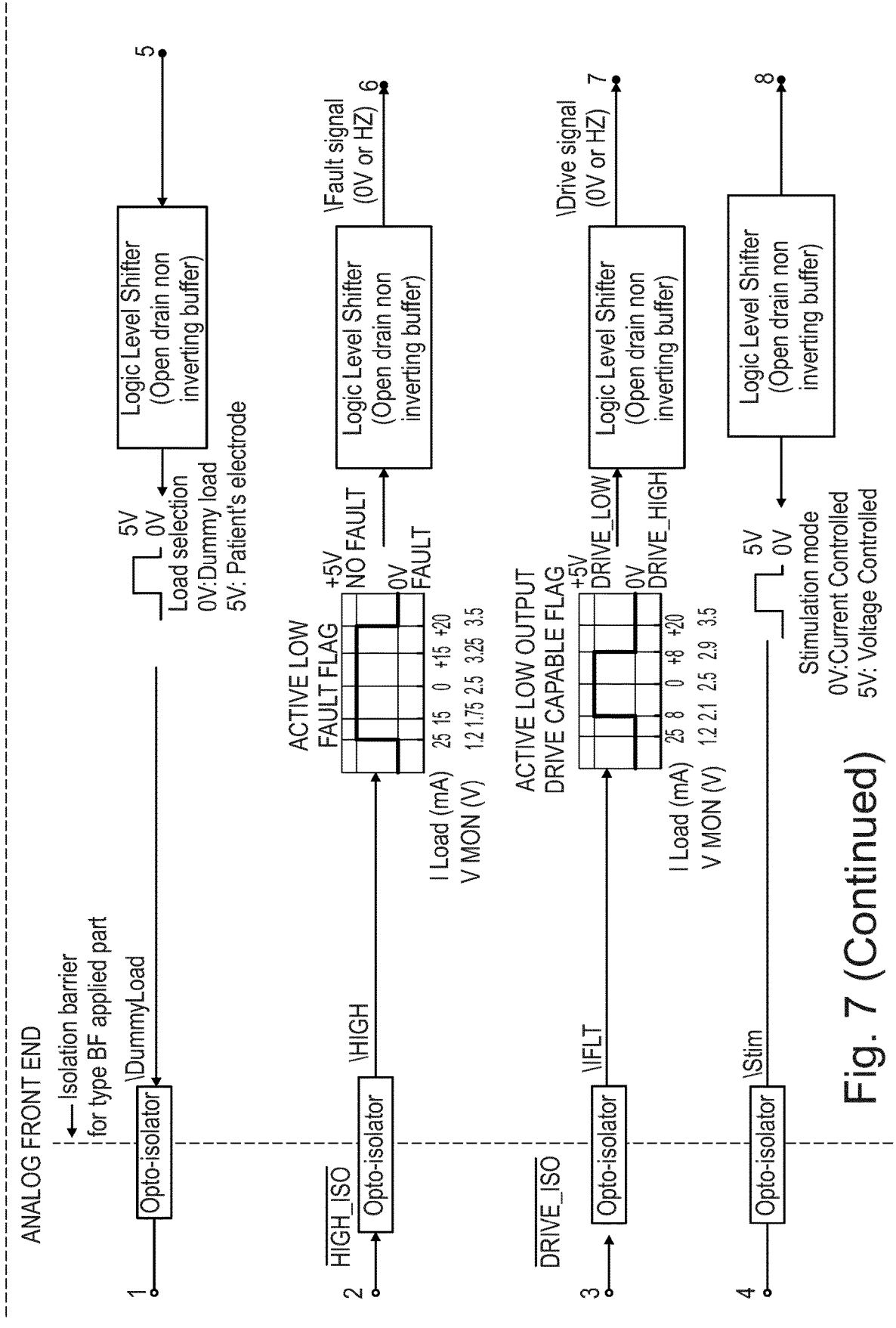
Figure 7:
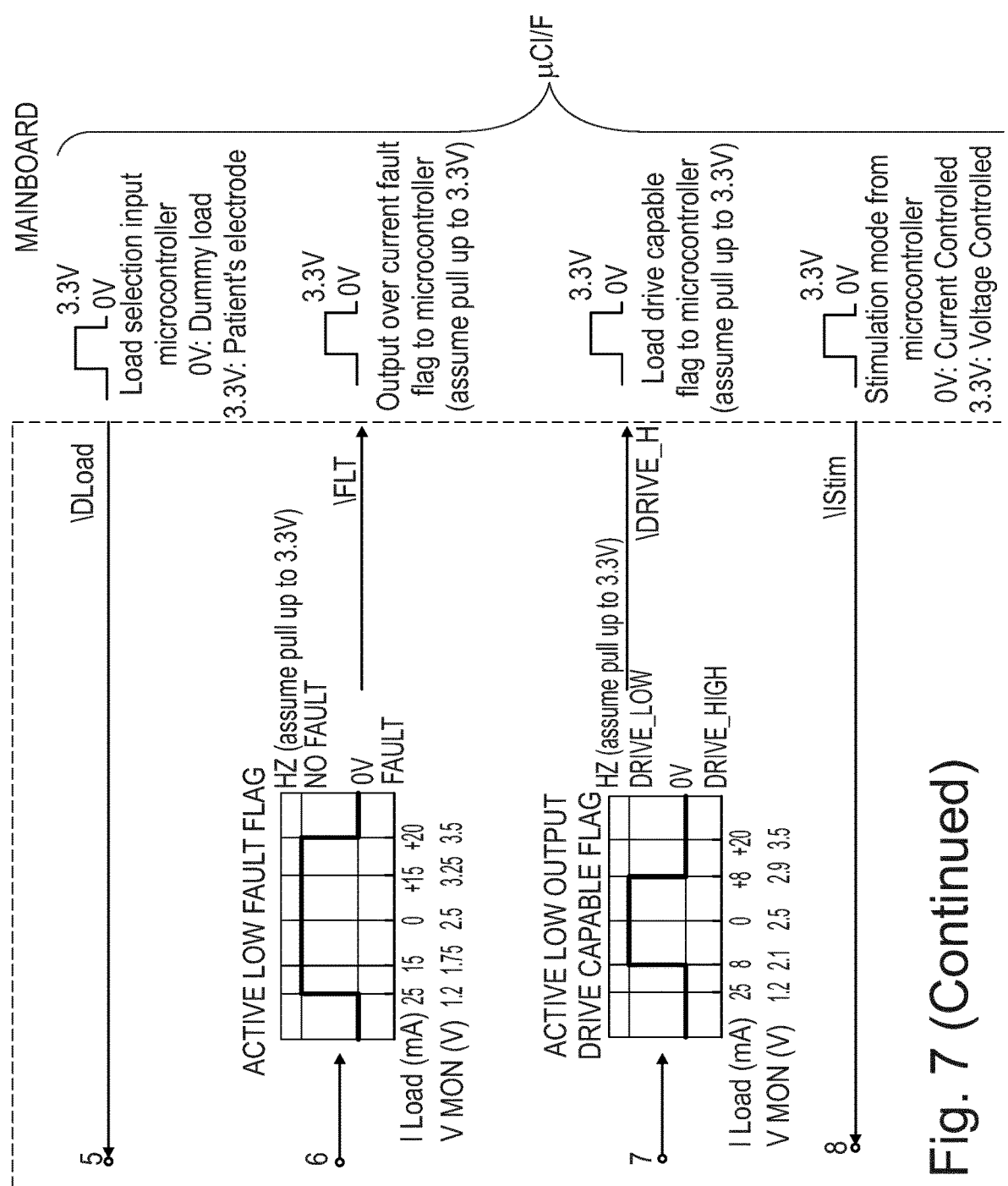
Figure 7:
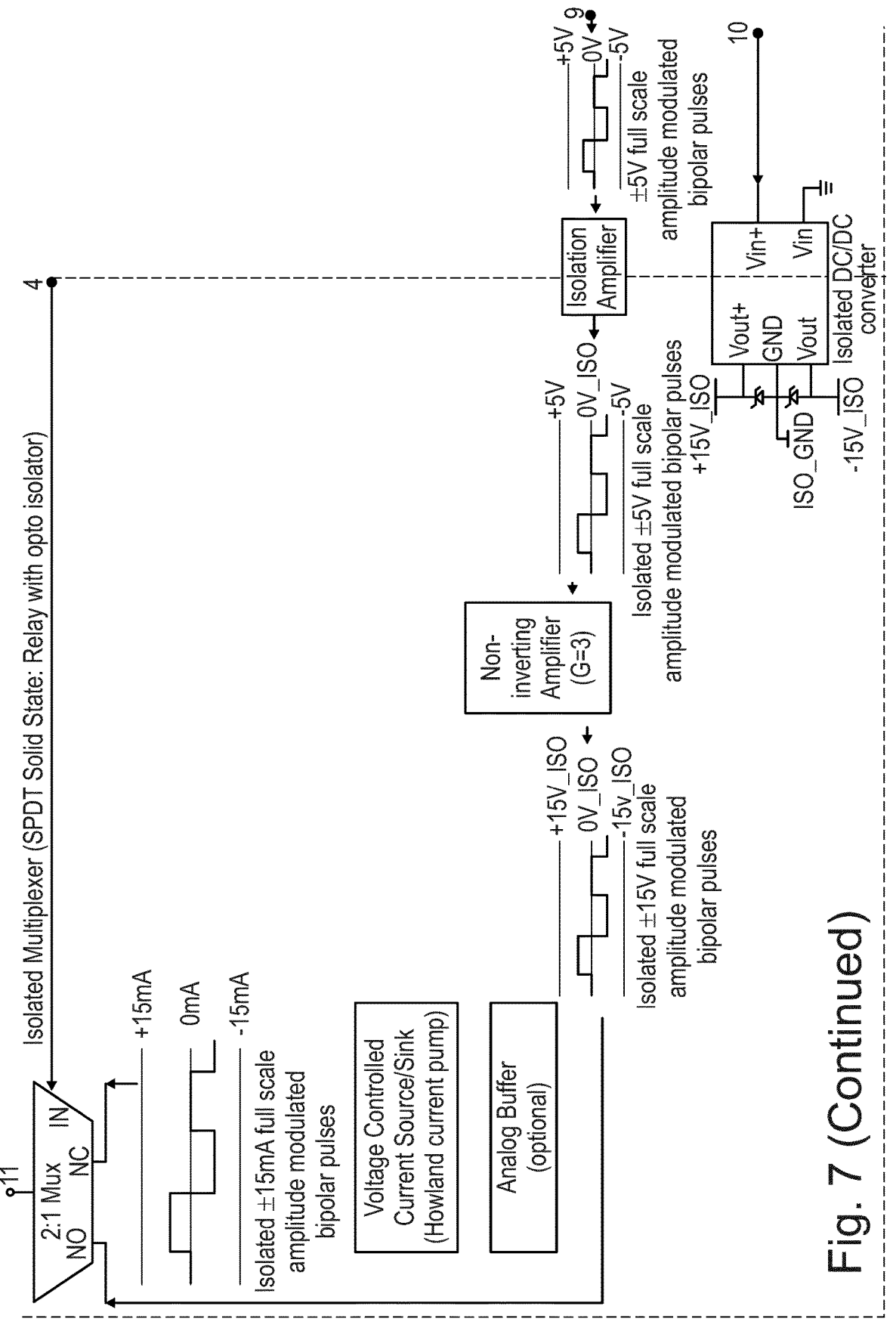
Figure 7:
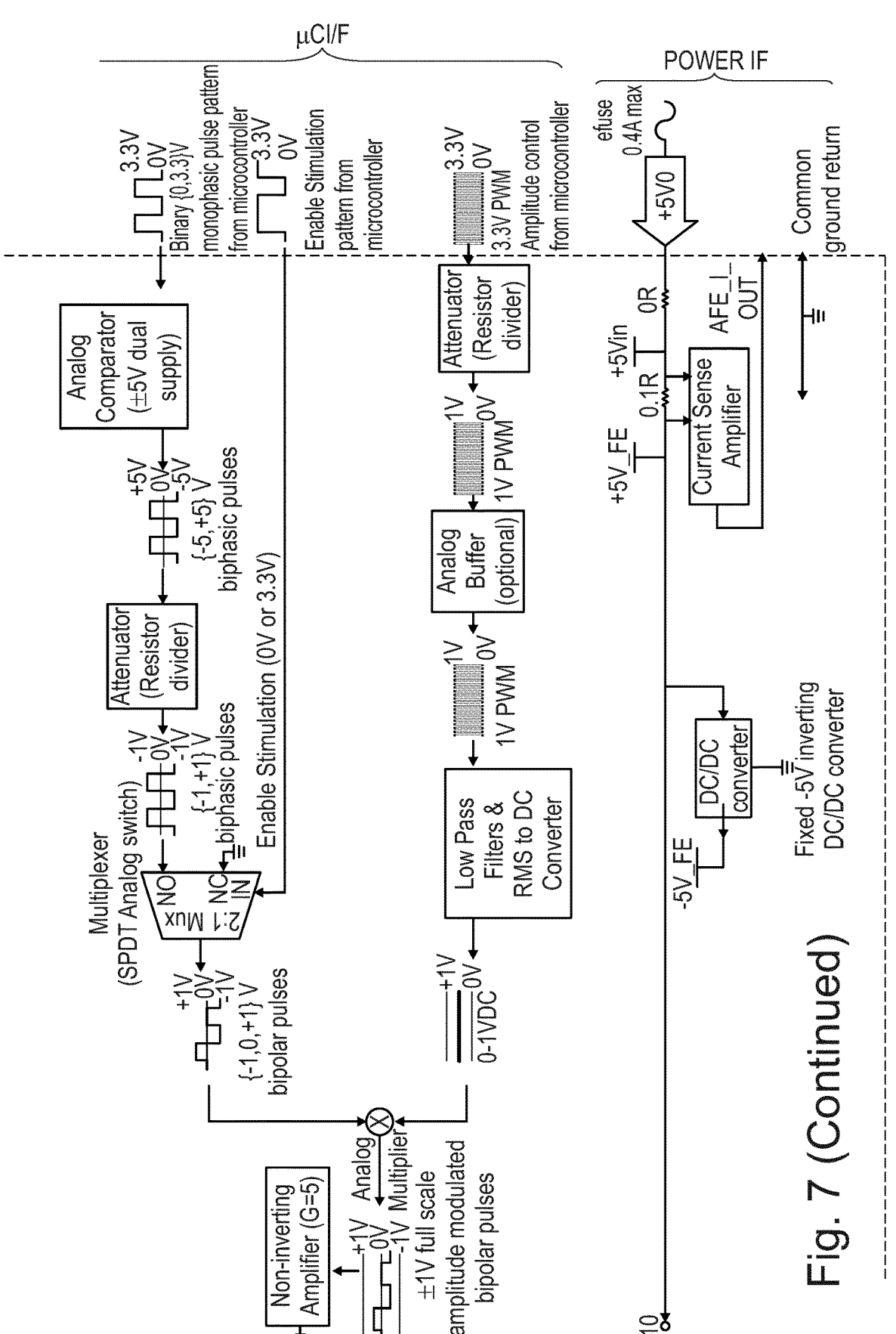

Referring now to FIG. 7, there is shown a high-level circuit schematic of an example stimulation generator according to the disclosure. The inputs and outputs to a digital controller such as a microcontroller are shown on the right of the figure. The outputs to the patient electrodes are shown at the left. A pulse pattern input comprising a binary monophasic pulse pattern from 0 to 3.3 volts is shown being fed to an analog comparator. The 0 to 3.3 Volt supply is compared to a ±5 volt supply such the that the output of the analog comparator is a stream of bipolar pulses from −5 V to +5 V. Next the signal is fed to an attenuator such as a resistor divider from which the output is a stream of bipolar pulses having an amplitude of ±1 V. This signal is fed to the normally open input of a 2:1 multiplexer. The normally closed input is connected to ground. The enable signal from the microcontroller is connected to the selecting output of selecting input of the multiplexer. In this way a stream of bipolar pulses having a desired mark space ratio is output from the multiplexer. This output has a magnitude of ±1 V, this fed to an analog multiplier. Simultaneously, a 3.3 V pulse width modulated amplitude control signal is also received from the microcontroller. The PWM signal is attenuated to a 0 V to 1 V signal and then put through an optional analog buffer. Next, this signal is put through a converter to create an analogue signal. The converter may comprise low pass filters and an RMS-to-DC converter. The output of the converter is an analogue signal having a magnitude of 0 V to 1 Volt DC. This analogue signal is also fed to the analog multiplier.

The analogue multiplier multiplies the analogue signal and the bipolar signal to create a ±1 V full scale amplitude modulated bipolar pulse signal. This signal is put through a non-inverting amplifier having a gain of five to provide a ±5Vfull scale amplitude modulated bipolar pulse signal. Next the signal is amplified again, with a gain of three, to provide a ±15 V full scale amplitude modulated bipolar pulse signal. This signal may be considered to correspond to the preliminary output voltage signal described previously herein.

The ±15 V full scale amplitude modulated bipolar pulse signal is supplied to the normally open input a 2:1 multi-plexor, and simultaneously to voltage-controlled current source/sink via an option analog buffer. This current source outputs a ±15 mA full scale output modulated pulse signal, which is fed to the normally closed input of the multiplexor. The select input of the multiplexor is fed to the select input of the multiplexor. The output signal of the multiplexor passes through a capacitor, a current sensing resistor and a polyfused before being fed to a final multiplexor. The final multiplexor allows the stimulation signal to be diverted to a dummy load for diagnostic uses.

A current sense amplifier is connected across the current sense resistor to a pair of parallel open-drain voltage detectors. These provide a "load over current fault" flag to the microcontroller, and an "output drive capable flag".

The circuit shown in FIG. 7 is suitable for use in a percutaneous device and as such includes electrical isolation. In an implanted or injected device no such isolation is required.

Figure 8:
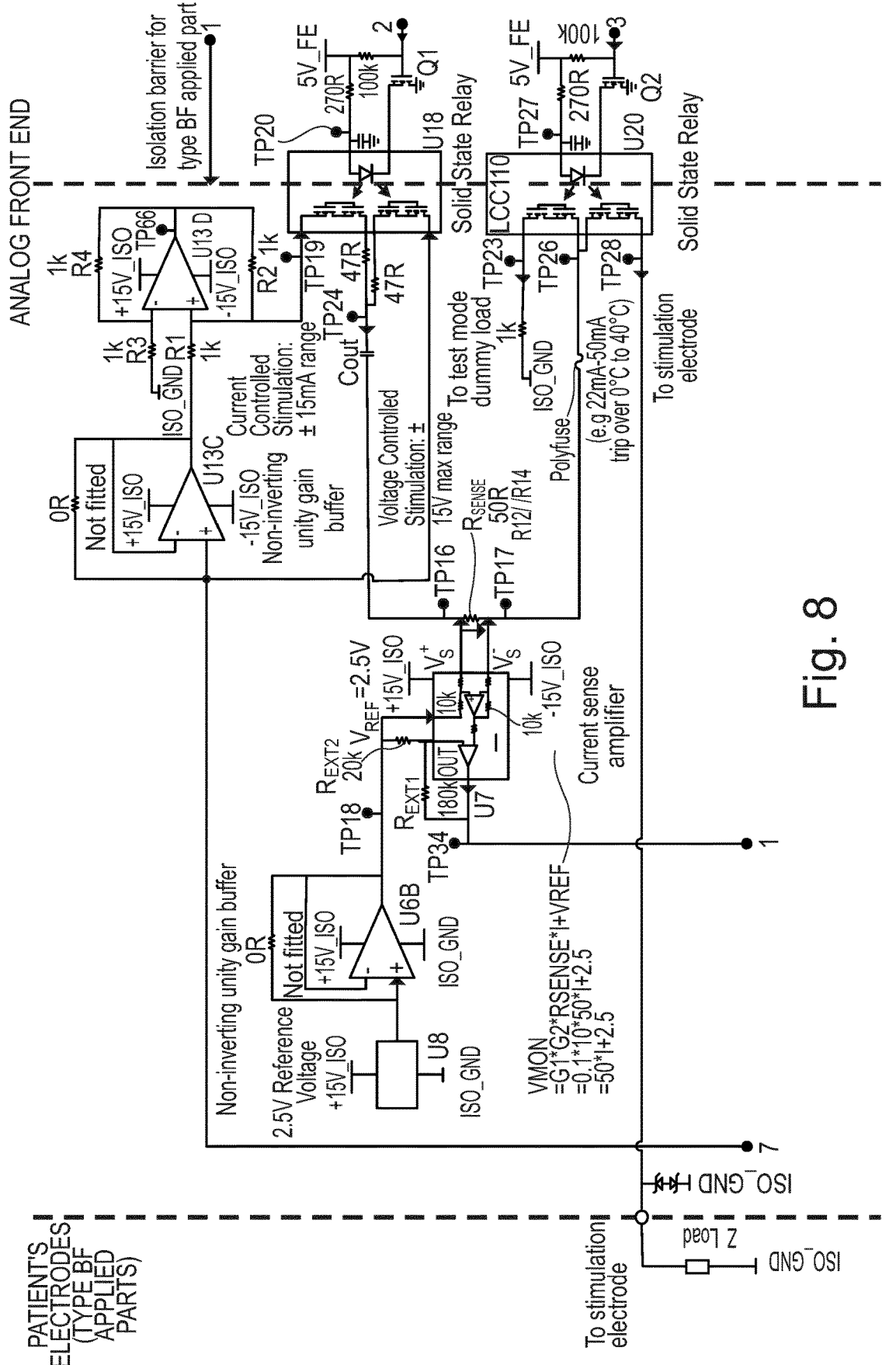
FIG. 8 is a circuit schematic of an example stimulation generator according to the disclosure.
Figure 8:
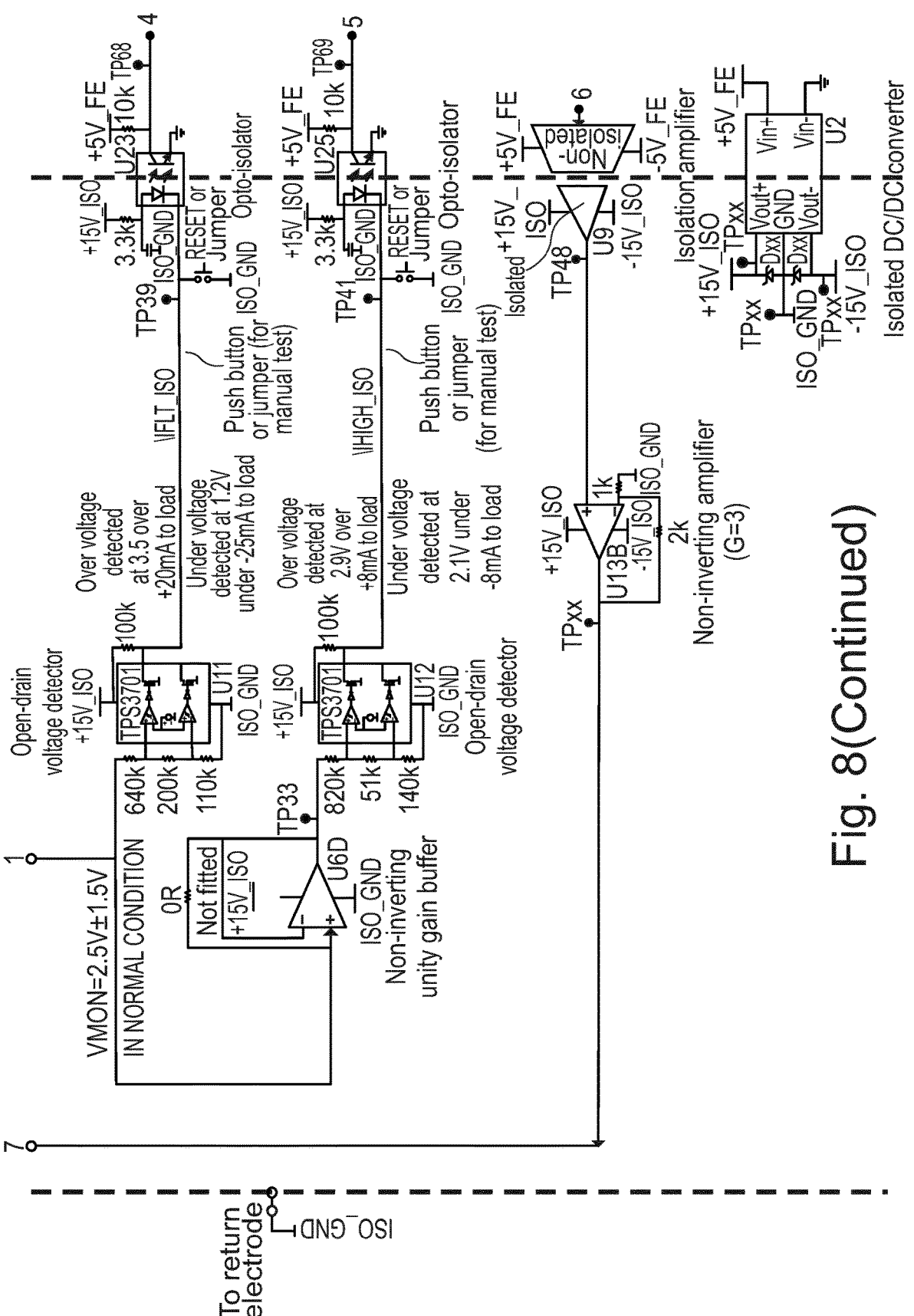
Figure 8:
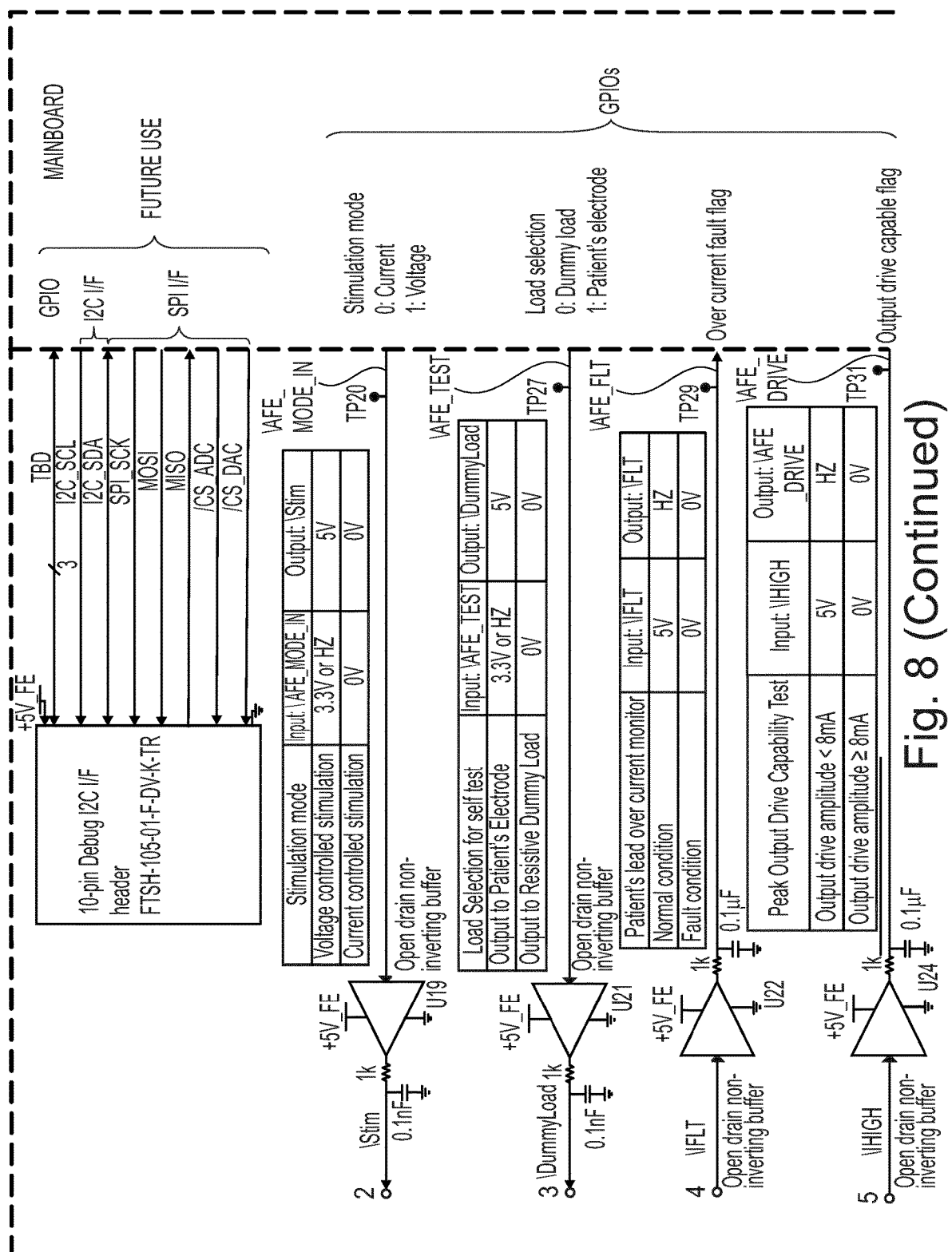
Figure 8:
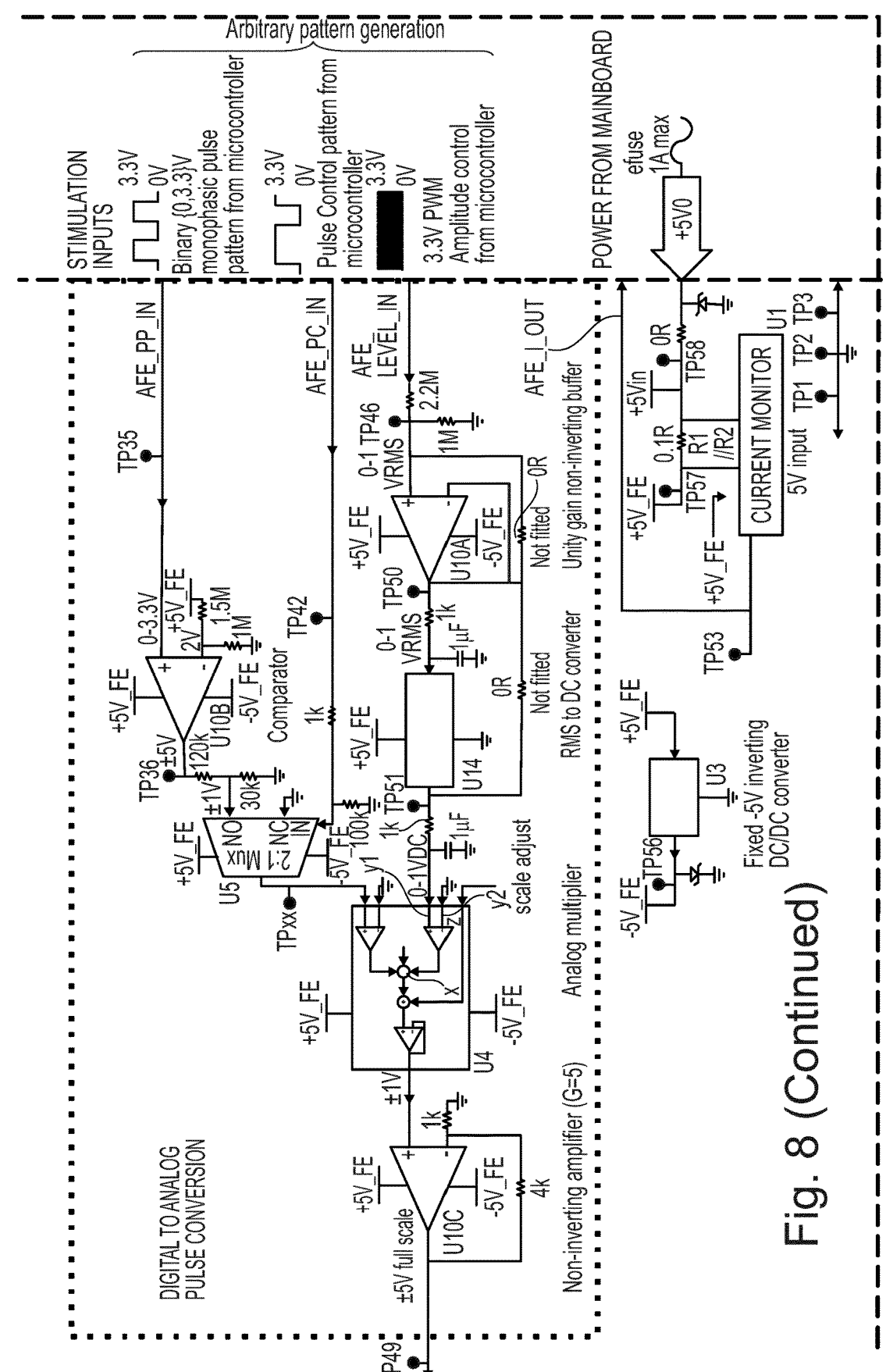

Referring to FIG. 8 is a circuit schematic of an example stimulation generator corresponding to that shown in FIG. 7.

Figure 9:
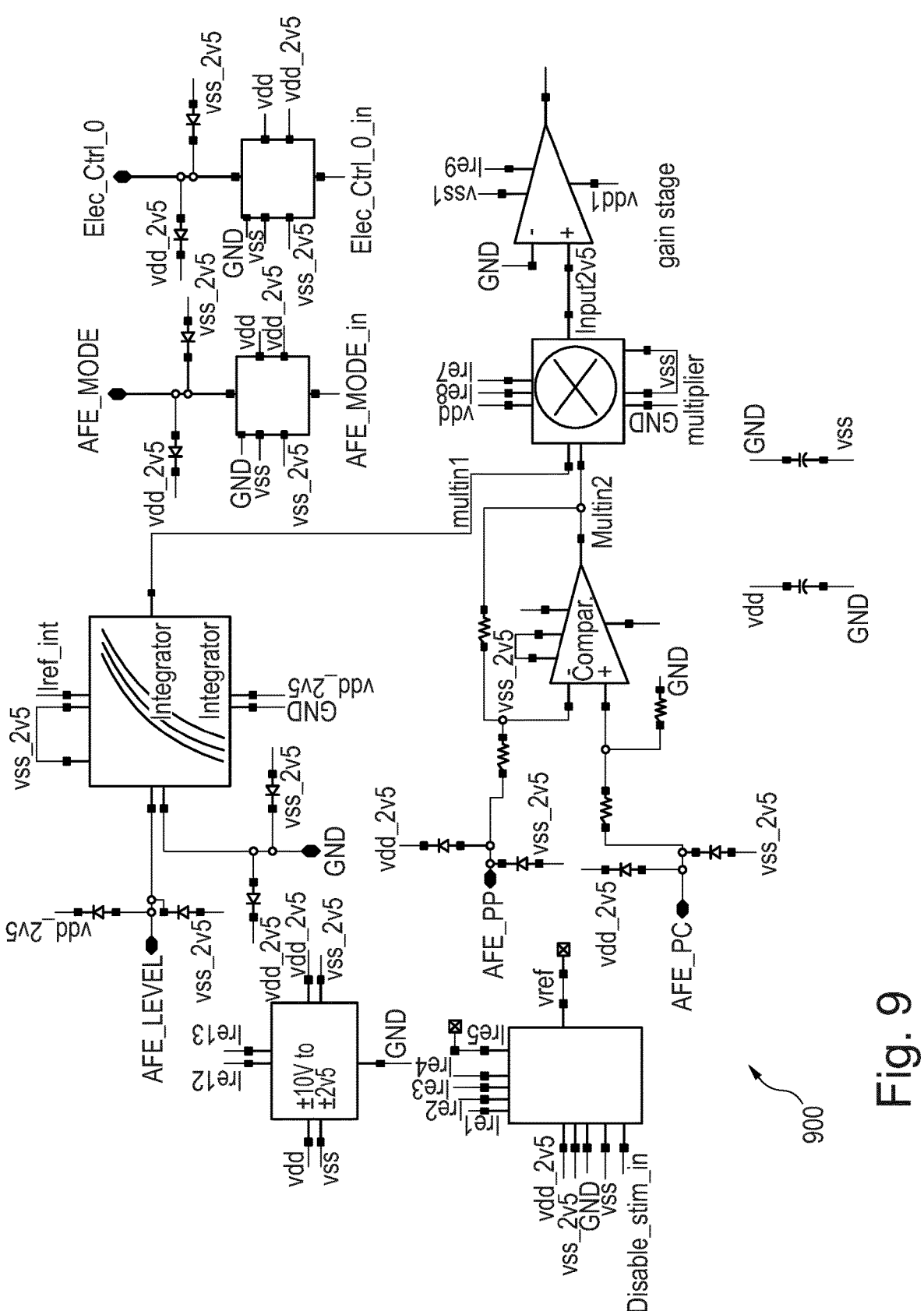
FIG. 9 is a is a high-level circuit schematic of a further example stimulation generator according to the disclosure.
Figure 9:
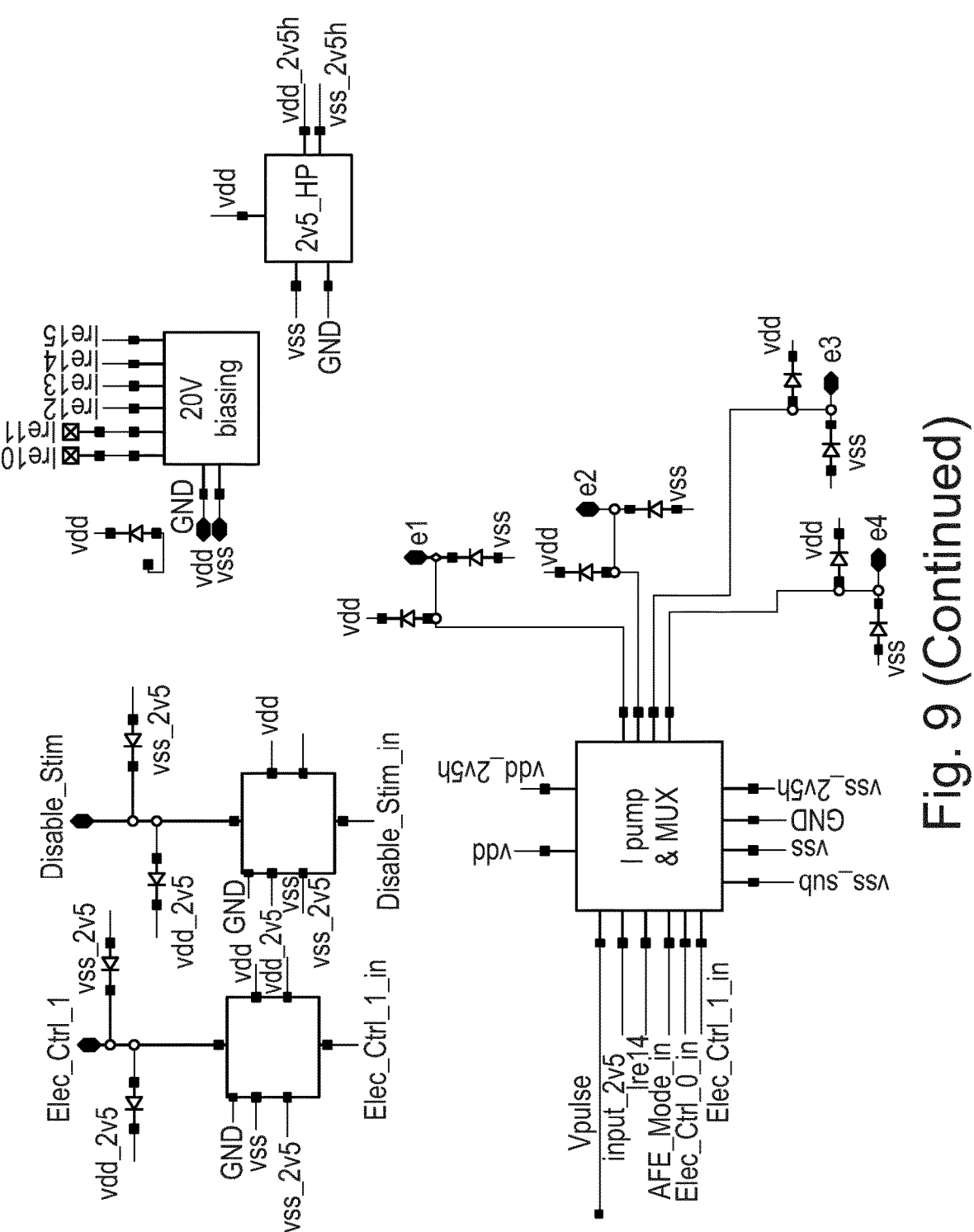

Referring now to FIG. 9, there is shown a high-level circuit schematic of a further example stimulation generator according to the disclosure. The stimulation generator of FIG. 9, indicated generally by the reference numeral 900, may be used to provide stimulation via four electrodes, to be connected to contacts labelled e1, e2, e3 and e4 respectively. The stimulation generator 900 comprises an input contact labelled AFE_LEVEL for receiving the amplitude control signal; an input contact labelled AFE_MODE for receiving the stimulation mode signal; an input contact labelled AFE_PP for receiving a pulse pattern signal; and an input contact labelled AFE_PC for receiving a pulse control signal, which may also be referred to as an enable signal. The stimulation generator 900 further comprises two power inputs, vdd and vss (±10 V), a ground contact, and three control contacts. The first control contact is labelled Disable_Stim which receives a signal to switch off/on the whole stimulation generator 900. The other control contacts are labelled Elec_Ctrl_0 and Elec_Ctrl_1 are for use in selecting which of the four electrodes e1, e2, e3, e4 is to receive for stimulation signal. The AFE_MODE contact may be a control contact rather than an input contact.

The pulse width modulated amplitude control signal received at AFE_LEVEL passes through an integrator cir-cuit which produces around −1 V. The integrator circuit may be an op-amp integrator. The integrator circuit provides an RMC to DC conversion of the amplitude control signal. The output of the integrator, labelled multin1, is one of the inputs to a four-quadrant multiplier circuit, labelled multiplier. The binary pulse pattern signal and binary pulse control signal received at AFE_PP and AFE_PC respectively are combined via the output difference amplifier circuit, comprising an op-amp labelled Compar to create the biphasic pulses of the duty cycle signal, labelled Multin2. The use of the op-amp circuit to combine these signals is both spatially and power efficient. The output of the multiplier is fed through a gain stage and to create the preliminary output voltage signal, labelled Vpulse. The four-quadrant multiplier enables the conversion of digital inputs "AFE_PP", "AFE_PC" and "AFE_LEVEL" into analog pulses of controlled amplitude, duration and repetition rate.

The Vpulse signal is then fed into a combined voltage-controlled current source and multiplexor, labelled I pump & MUX, which provides the stimulation signal to the contacts e1, e2, e3, and e4 for the electrodes. A contact of the I pump & MUX module receives a signal derived from the stimu-lation mode signal labelled AFE_MODE to control the stimulation mode of the stimulation signals provided to the contacts e1, e2, e3, e4 for the electrodes. The voltage-controlled current source may be implemented as a Howland pump. The Howland pump and the op-amp gain stages are used to produce high current and voltages to be delivered to the dedicated electrodes. The combination of the Howland Pump and multiplexor in the I pump & MUX module allows for completely turning off the current mode stimulations in high voltage devices, and also accommodates the loading effects of high voltage devices between the Howland pump and gain stage. The combination of the voltage-controlled current source and the multiplexor are shown in more detail in FIG. 10.

The output of four quadrant multiplier is controlled by AFE_MODE for voltage and current stimulations at the four electrodes (e1, e2, e3 and e4) by the selection from Elec_C-trl_0 and Elec_Ctrl_1 in a 2-to-4 decoder block, that forms part of the combined voltage-controlled current source and multiplexor I pump & MUX module.

Figure 10:
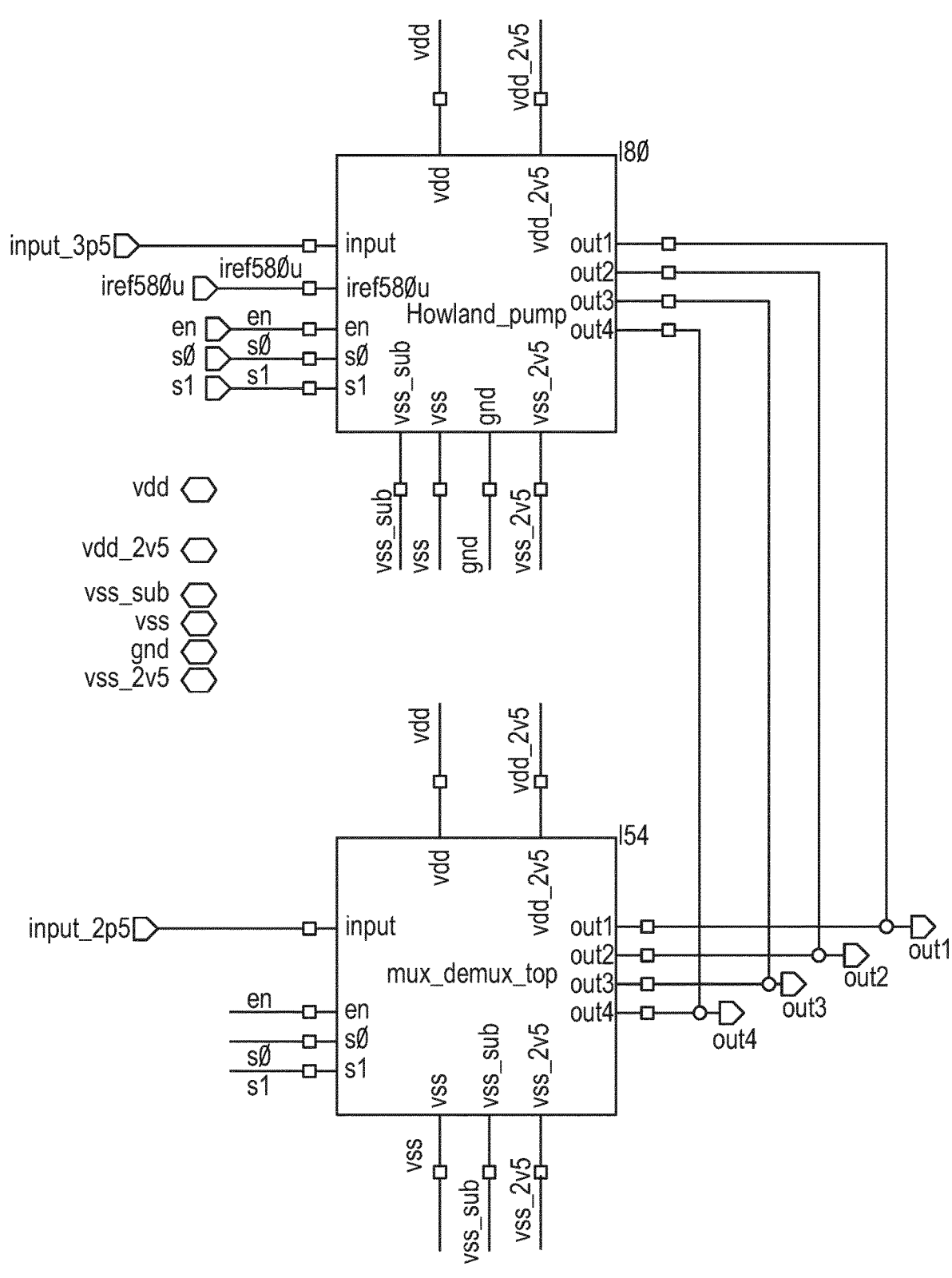
FIG. 10 is a is a high-level circuit schematic of a combination of a voltage-controlled current source and multiplexor, for use in a stimulation generator according to the disclosure.

The circuits illustrated in FIGS. 7 and 9 may be implemented as an Application Specific Integrated Circuit (ASIC) to facilitate a small form factor, allowing a neurostimulator small enough for injection. Referring now to FIG. 10, there is shown a block diagram of a stimulation ASIC 910 corresponding to stimulation generator 900 of FIG. 9. The contacts of the stimulation ASIC 910 are labelled in accordance with the labelling of the stimulation generator 900 in FIG. 9. The stimulation ASIC 910 is labelled as afe_top_kiwi_c2_disable in the figure. The stimulation ASIC 910 may be implemented in Taiwan Semiconductor Manufacturing Company TSMC 180 nm BCD high voltage node. Aspects of the stimulation ASIC 910 may be implemented using 5V CMOS devices. For example, the integrator, the four-quadrant multiplier, the voltage-controlled current source and the multiplexor may be implemented in this manner.

Table 1 comprises details of the pin-out of the stimulation ASIC 910, listing the 14 contacts and their functionality and control. For pins 1 to 7, while the absolute maximum voltage ratings relative to ground are −1.1V to 4.4V, the expected nominal input range is 0V to 3.3V.

including number of pins/contacts must be considered in the design and choice of each component including the stimulation generator. Similarly, the manner in which the characteristics of the desired stimulation signal are conveyed from the microcontroller to the stimulation generator should be considered carefully. In the stimulation generators disclosed herein, only 3 or 4 inputs are required from the microcontroller to provide the highly configurable stimulation signal.

In use, the neurostimulator 950 may be implanted or injected, into a patient, with one or more electrodes positioned appropriately with respect to the nerves to be treated. The neurostimulator 950 can then generate desired stimulation signals as described herein for the treatment of the patient's symptoms. The neurostimulator may be suitable for positioning into a patient by means of an injection. As such, it will be understood that the neurostimulator and its components must be implemented to fit a small form factor. In examples, the neurostimulator may have a diameter of between about 0.5 millimetres and about 5 millimetres, for example between about 1 millimetre and about 3 millimetres. In an example, the neurostimulator device has a diameter of 2.9 mm. The neurostimulator may have a length of up to about 10 millimetres, for example up to about 5 millimetres.

TABLE 1

| Pin Number | Name | Type | Description | Absolute Maximum Voltage Ratings relative to GND |
|---|---|---|---|---|
| 1 | AFE_LEVEL | Input | Amplitude control from microcontroller pulse width modulator | −1.1 V to 4.4 V |
| 2 | AFE_PP | Input | Enable Stimulation pattern from microcontroller | −1.1 V to 4.4 V |
| 3 | AFE_PC | Input | Binary {0, 3.3}V monophasic/biphasic pulses pattern from microcontroller | −1.1 V to 4.4 V |
| 4 | Disable_Stim | Input | Binary {0, 3.3}V on/off the whole chip from microcontroller | −1.1 V to 4.4 V |
| 5 | AFE_MODE | Input | Binary {0, 3.3}V voltage/current pulse pattern from microcontroller | −1.1 V to 4.4 V |
| 6 | Elec_Ctrl_0 | Input | Binary {0, 3.3}V selection of electrode on/off from microcontroller | −1.1 V to 4.4 V |
| 7 | Elec_Ctrl_1 | Input | Binary {0, 3.3}V selection of electrode on/off from microcontroller | −1.1 V to 4.4 V |
| 8 | vdd | Power | 10 V supply voltage | +6 V to +16 V |
| 9 | vss | Power | −10 V supply voltage | −16 V to +6 V |
| 10 | gnd | Ground | PCB ground. | N/A |
| 11 | e1 | Output | Voltage/current mode output to electrode 1. | −11.5 V to +11.5 V |
| 12 | e2 | Output | Voltage/current mode output to electrode 2. | −11.5 V to +11.5 V |
| 13 | e3 | Output | Voltage/current mode output to electrode 3. | −11.5 V to +11.5 V |
| 14 | e4 | Output | Voltage/current mode output to electrode 4. | −11.5 V to +11.5 V |

Figures 11, 12:
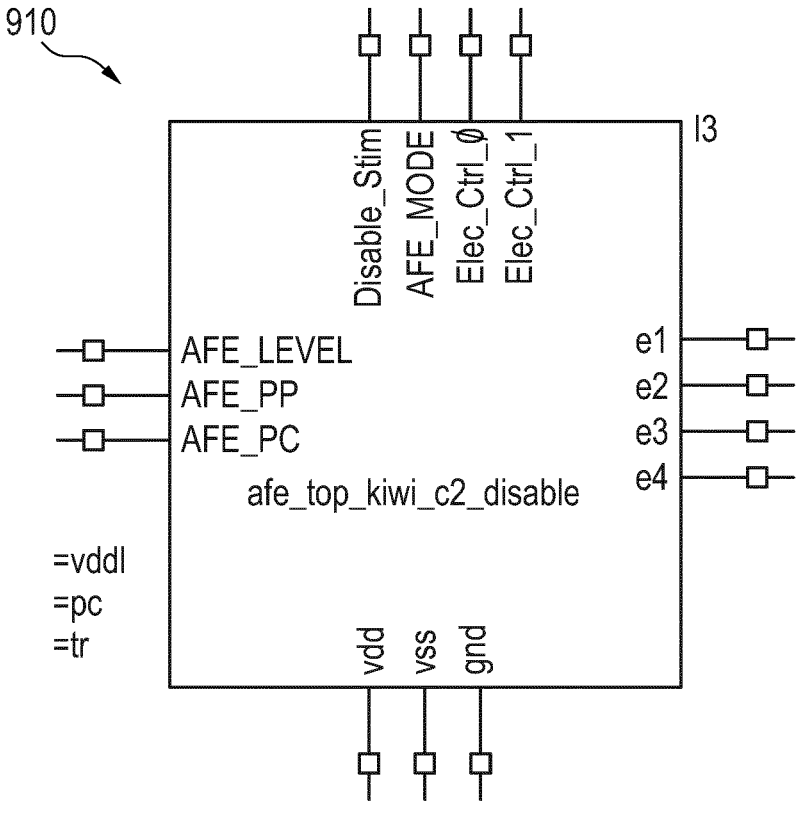
FIG. 11 is a diagram of a pin-out of an application specific integrated circuit for the stimulation generator of FIG. 9.
FIG. 12 is a block diagram of an example neurostimulator according to the disclosure.

Referring now to FIG. 12, there is a shown block diagram of an example of a neurostimulator comprising a stimulation generator according to the present disclosure. In FIG. 12, there is shown a neurostimulator 950 comprising a processor 952 such as a microcontroller; a power supply 954; an electrode 956; and a stimulation generator according to the present disclosure, such as the stimulation generator described herein in relation to FIGS. 1, 3, 5, 6, 7, 8, 9. A suitable microcontroller may be one from the MAXIM MAX32600 microcontroller family, the MAXIM MAX32660 microcontroller family, or similar devices. With the aim of providing an injectable device, it will be understood that the constraints of power consumption and size, In examples, the electrode may be in the form of an electrode lead, which may have a diameter of between about 0.3 millimetres to about 1.5 millimetres, for example between about 0.5 millimetres and 1.3 millimetres. The electrode lead may have a length of up to about 100 millimetres, for example up to about 50 millimetres, for example about 50 millimetres. However, it will be appreciated that the length of the electrode lead would correspond to the anatomy surrounding the targeted nerve, so a shorter or longer electrode lead may be appropriate depending on the depth of the nerve within the muscle tissue.

Figure 13:
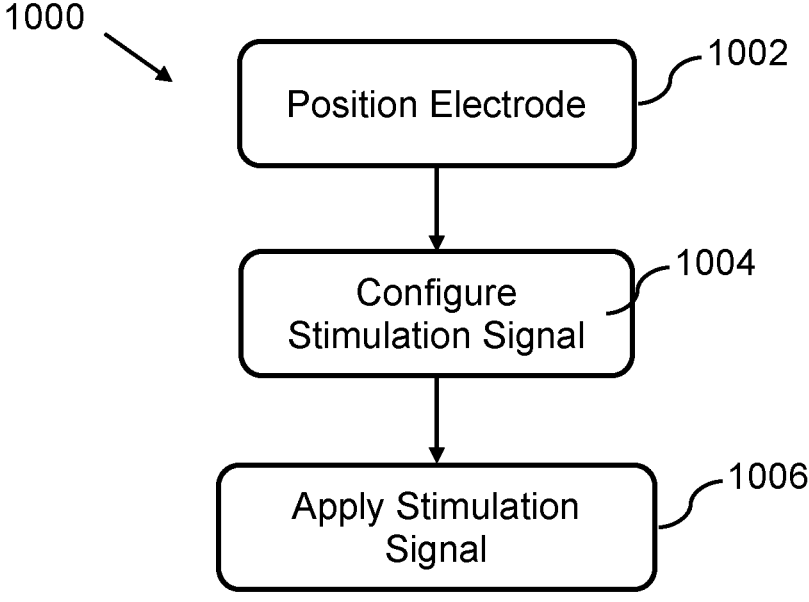
FIG. 13 is a flow chart of a method of treatment using a neurostimulator according to the disclosure.

Referring now to FIG. 13, there is shown a flow chart of a method of treatment, indicated generally by the reference numeral 1000 using a neurostimulator according to the present disclosure. At block 1002, the neurostimulator is injected into the patient with the electrode position as appropriate in relation to the area to be treated. The area to be treated may be a nerve, nerve bundle or other suitable area. At block 1004, the desired stimulation signal is configured by a user such as a clinician. At block 1006, the stimulation signal is applied to the area to be treated.

The invention comprises a front end neurostimulator signal generator capable of producing multiple types of electrical stimuli, including voltage-regulated and current-regulated outputs. The electrical stimulus can be combined with controllable noise signals of adjustable frequency and signal to noise ratio. This multimodal electrical stimulus architecture enables the device to cater for a wider range of patients and chronic pain conditions than existing neurostimulators limited to either current regulated outputs or voltage regulated outputs. The superposition of adjustable noise signals to the stimulation pattern contributes to the prevention of therapy tolerance and habituation that may lead to therapy failure over time.

The present invention relates to a stimulation generator suitable for use in an implantable neurostimulator, including an injectable neurostimulator. The stimulation generator is adapted to provide a configurable stimulation signal comprising a component, such as a pulse. The stimulation generator comprises circuitry to receive and combine an amplitude control signal and a duty cycle signal to produce a preliminary output voltage signal which includes the component of the stimulation signal. It further comprises a voltage-controlled current source adapted to be driven by the preliminary output voltage signal; and a mode selector controlled by a stimulation mode signal to output the component from the preliminary output voltage signal as a current-controlled component of the stimulation signal via the voltage-controlled current source or as a voltage-controlled component of the stimulation signal. The stimulation generator of the disclosure is particularly suited for implementation in a small form factor so that it may be placed in a patient by injection, thus avoiding the need for a surgical procedure to implant a device.

Throughout the description, the terms "voltage-controlled" and "voltage-regulated" may be understood to be interchangeable, similarly the terms "current-controlled" and "current-regulated".

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise. Throughout the description and claims of this specification, steps are not required to be taken in the order described.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A stimulation generator suitable for use in an injectable neurostimulator, the stimulation generator adapted to provide a configurable periodic stimulation signal comprising a component, the stimulation generator comprising:
   an input configured to receive digital voltages to generate the component including digital voltages representing:
      a stimulation mode signal to configure the component of the stimulation signal as a voltage-controlled component or a current-controlled component,
      an amplitude control signal to control the amplitude of the component of the stimulation signal, and
      a duty cycle signal to control the duration of the component of the stimulation signal;
   a converter to convert the amplitude control signal to an analog signal;
   a combining module to combine the duty cycle signal with the analog signal to provide a preliminary output voltage signal which includes the component of the stimulation signal;
   a voltage-controlled current source adapted to be driven by the preliminary output voltage signal; and
   a mode selector adapted to be controlled by the stimulation mode signal to select to output the component from the preliminary output voltage signal as a current-controlled component of the stimulation signal via the voltage-controlled current source or as a voltage-controlled component of the stimulation signal.

2. A stimulation generator as claimed in claim 1 adapted to provide a configurable periodic stimulation signal comprising the voltage-controlled component and the current-controlled component.

3. A stimulation generator as claimed in claim 1 wherein the duty cycle signal and the analog signal are scaled to have a maximum magnitude of 1 V prior to being input to the combining module.

4. A stimulation generator as claimed in claim 1 wherein the output of the combining module is amplified to provide the preliminary output voltage signal.

5. A stimulation generator as claimed in claim 1 wherein the combining module is an analog multiplier.

6. A stimulation generator as claimed in claim 1 further comprising a noise input signal adapted to introduce stochastic noise to the stimulation signal as an input to the combining module.

7. A stimulation generator as claimed in claim 6 the combining module is an analog multiplier and wherein the noise input signal is applied to a scale adjust input of the combining module.

8. A stimulation generator as claimed in claim 1 further comprising a current management module for managing an output current of the stimulation signal, the current management module comprising a combination of a polyfuse, current limiting resistors and circuitry adapted to generate an active low fault flag to a microcontroller if the output current is outside a predefined range.

9. A stimulation generator as claimed in claim 1 wherein the period of the stimulation signal is in the range 2.5 μs to 2 ms.

10. A stimulation generator as claimed in claim 1 wherein the component has duration of between 1.25 μs and 2 ms.

11. A stimulation generator as claimed in claim 1 wherein the amplitude of the stimulation signal can change at a rate of up to 25 kHz.

12. A stimulation generator as claimed in claim 1 wherein the mode of the stimulation signal can change at a rate of up to 400 KHz.

13. A stimulation generator as claimed in claim 1 wherein the input is configured to receive the digital voltages to generate the component in parallel.

14. An injectable neurostimulator comprising a processor, a power supply, an electrode, and the stimulation generator of claim 1.

15. An injectable neurostimulator as claimed in claim 14 wherein the processor comprises one output connection for each of the digital voltages to be received by the stimulation generator.

16. A method for generating a stimulation signal for use in neurostimulation, wherein the method comprises:

receiving digital voltages for generating a component including digital voltages representing:

a stimulation mode signal to configure the component of the stimulation signal as a voltage-controlled component or a current-controlled component, an amplitude control signal to control the amplitude of the component of the stimulation signal, and a duty cycle signal to control the duration of the component of the stimulation signal;

converting the amplitude control signal to an analog signal;

combining the duty cycle signal with the analog signal to provide a preliminary output voltage signal which includes the component of the stimulation signal;

driving a voltage-controlled current source by the preliminary output voltage signal; and outputting the component from the preliminary output voltage signal as a current-controlled component of the stimulation signal via the voltage-controlled current source or as a voltage-controlled component of the stimulation signal, based on the stimulation mode signal.

17. The method as claimed in claim 16 wherein combining the duty cycle signal with the analog signal comprises multiplying the duty cycle signal by the analog signal using an analog multiplier.

18. The method as claimed in claim 16 further comprising introducing stochastic noise to the stimulation signal by combining a noise input signal with the duty cycle signal with the analog signal.

19. The method as claimed in claim 18 wherein the introducing the stochastic noise to the stimulation signal comprises applying the noise input signal to a scale adjust input of an analog multiplier which is combining the duty cycle signal with the analog signal.

* * * * *